(12) United States Patent
McChesney et al.

(10) Patent No.: US 8,912,229 B2
(45) Date of Patent: Dec. 16, 2014

(54) TAXANE AND ABEO-TAXANE ANALOGS

(75) Inventors: James D. McChesney, Etta, MS (US); John T. Henry, Longmont, CO (US); Sylesh Venkataraman, Broomfield, CO (US); Mahesh Kumar Gundluru, Cordova, TN (US)

(73) Assignee: Arbor Therapeutics, LLC, Etta, MS (US)

( * ) Notice: Subject to any disclaimer, the term of this patent is extended or adjusted under 35 U.S.C. 154(b) by 0 days.

(21) Appl. No.: 14/110,423

(22) PCT Filed: Apr. 6, 2012

(86) PCT No.: PCT/US2012/032568
§ 371 (c)(1),
(2), (4) Date: Dec. 10, 2013

(87) PCT Pub. No.: WO2013/106029
PCT Pub. Date: Jul. 18, 2013

(65) Prior Publication Data
US 2014/0093503 A1    Apr. 3, 2014

Related U.S. Application Data

(60) Provisional application No. 61/472,968, filed on Apr. 7, 2011.

(51) Int. Cl.
*A61K 31/35*     (2006.01)
*A61K 31/335*    (2006.01)
*C07D 309/00*    (2006.01)
*C07D 407/00*    (2006.01)
*A61K 31/357*    (2006.01)
*C07D 493/06*    (2006.01)
*C07D 493/04*    (2006.01)
*A61K 45/06*     (2006.01)

(52) U.S. Cl.
CPC ............ *C07D 493/06* (2013.01); *A61K 31/357* (2013.01); *C07D 493/04* (2013.01); *A61K 45/06* (2013.01)
USPC ........... 514/453; 514/449; 514/357; 549/510; 549/511; 549/357; 549/358

(58) Field of Classification Search
None
See application file for complete search history.

(56) References Cited

FOREIGN PATENT DOCUMENTS

WO    WO 2005030150 A2 *  4/2005
WO    WO 2008121476 A1 * 10/2008

* cited by examiner

*Primary Examiner* — Jeffrey S. Lundgren
*Assistant Examiner* — Michael Schmitt
(74) *Attorney, Agent, or Firm* — Sam L. Nguyen; Hamilton Desanctis & Cha, LLP

(57) ABSTRACT

The present application discloses new taxane analogs, intermediates and methods for producing them. The present application is also directed to pharmaceutical formulations comprising abeo-taxanes and methods of treating cancer with the abeo-taxanes.

5 Claims, 7 Drawing Sheets

TAXANE AND ABEO-TAXANE ANALOGS

CROSS-REFERENCE TO RELATED APPLICATION

This application is a U.S. national stage of PCT Application No. PCT/2012/032568 with an international filing date of 6 Apr. 2012, which claims the benefit of U.S. Provisional Patent Application Ser. No. 61/472,968, filed Apr. 7, 2011, the content of which is incorporated herein by reference in its entirety.

FIELD OF THE INVENTION

The present invention generally relates to chemical compounds for use in treating cancer patients. More particularly, the present invention is directed to new and useful taxane analogs and further to methods for producing them. The present application is also directed to pharmaceutical formulations comprising the disclosed taxanes, abeo-taxanes and methods of treating cancer with the disclosed taxanes, abeo-taxanes and their pharmaceutical formulations. In addition, the present application discloses 9α,10β- and 9α,10α-taxane and abeo-taxane analog syntheses and their applications in cancer treatment. Specifically, the present invention relates to taxane and abeo-taxane analogs, intermediates and their synthesis.

BACKGROUND OF THE INVENTION

Taxanes such as paclitaxel are diterpene natural product drug molecules that have been used to treat cancer in the clinic for many years. Synthetic analogs of paclitaxel such as docetaxel have been developed and also used in the clinic to treat various cancers. The taxanes act by binding to tubulin and stabilizing the mitotic spindle thereby halting mitosis and leading cells into apoptosis. However the taxanes and other drug molecules have been found to be ineffective in treating multidrug resistant cancers and cancers with mutant tubulins. Therefore a continuing need exists for compounds that are effective therapeutic agents for cancers that are multidrug resistant.

One approach in developing new anti-cancer drugs is the identification of superior analogs and derivatives of biologically active compounds. Modifications of various portions of a complex molecule may lead to new and better drugs having improved properties such as increased biological activity, effectiveness against cancer cells that have developed multi-drug resistance (MDR), fewer or less serious side effects, improved solubility characteristics, better therapeutic profile and the like.

Zamir et al, Tetrahedron Letters, 37, 6435-6438 (1996) discloses taxane analogues containing a five membered A-ring and a position 1 —C(CH$_3$)$_2$OH group. These analogues were abeo-taxanes lacking the four membered oxetane ring. Zamir et al, Tetrahedron Letters, 53. 15991-16008 (1997) discloses abeo-taxane analogues and also trapped intermediates containing a 5 membered A-ring and a position 1 —C(CH$_3$)$_2$OH group. Wahl et al, Tetrahedron, 48, 6965-6974 (1992) discloses a wide range of modified taxane analogues including one which had a 5 membered A-ring and a 1 position —C(CH$_3$)$_2$OH group.

U.S. Pat. No. 5,352,806 discloses 10β-substituted taxanes which may have bridges between the 7- and 9-hydroxyl groups of the formula:

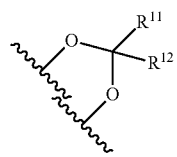

wherein $R^{11}$ and $R^{12}$ are as defined in the patent.

SUMMARY OF THE INVENTION

In view of the promising anti-tumor activity of the taxane family, it is desirable to investigate new and improved taxane analogs and derivatives for use in cancer treatment. One particularly important area is the development of drugs having improved MDR reversal properties. Accordingly, there is a need to provide new taxane compounds having improved biological activity for use in treating cancer. There is also a need to provide methods for forming such compounds. Finally, there is a need for methods of treating patients with such compounds in cancer treatment regimens. The present invention is directed to meeting these needs.

In one embodiment, the present application describes compounds that have an affinity to bind with tubulin and are potential drugs in the treatment of cancer and other disease conditions related to dysfunction of proteins associated with tubulin such as tau, MAP1, MAP2 and MAP4.

Embodiments and Aspects of the Application

The following embodiments, aspects and variations thereof are exemplary and illustrative and not intended to be limiting in scope.

In one embodiment, there is provided compounds of the formula I or II:

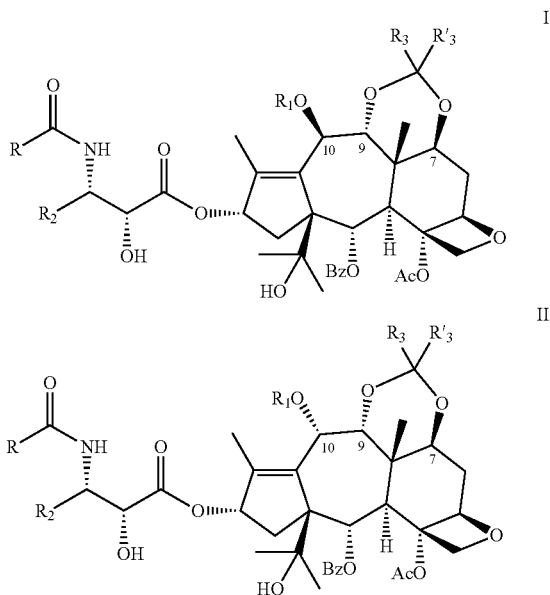

wherein: R is selected from the group consisting of C$_{1-6}$alkyl, C$_{1-6}$alkoxy-, C$_{2-6}$alkenyl, C$_{6-10}$aryl, C$_{6-10}$arylC$_{1-3}$alkyl and $C_{6-10}$aryl$C_{1-3}$alkoxy; $R_1$ is hydrogen or is selected from the group consisting of $C_{1-6}$alkyl, $C_{2-6}$alkenyl, R'CO—, $C_{6-10}$aryl and $C_{6-10}$aryl$C_{1-3}$alkyl, wherein R' is selected from the group consisting of $C_{1-6}$alkyl, $C_{6-10}$aryl and aryl$C_{1-3}$alkyl-; $R_2$ is selected from the group consisting of optionally substituted $C_{1-6}$alkyl, optionally substituted phenyl and optionally substituted heteroaryl; $R_3$ is hydrogen or is selected from the group consisting of $C_{1-18}$alkyl, $C_{2-6}$alkenyl, $C_{2-6}$alkynyl, $C_{6-10}$aryl and $C_{6-10}$aryl$C_{1-3}$alkyl, wherein each $C_{1-18}$alkyl, $C_{3-6}$alkenyl and $C_{3-6}$alkynyl are optionally substituted by 1 or 2 —OH, $NH_2$, —NH$C_{1-3}$alkyl or —N($C_{1-3}$alkyl)$_2$ and wherein each $C_{6-10}$aryl is unsubstituted or substituted with 1, 2 or 3 —OCH$_3$; R'$_3$ is hydrogen or is selected from the group consisting of $C_{1-18}$alkyl, $C_{2-6}$alkenyl, $C_{2-6}$alkynyl, $C_{6-10}$aryl and $C_{6-10}$aryl$C_{1-3}$alkyl, wherein each $C_{1-18}$alkyl, $C_{3-6}$alkenyl and $C_{3-6}$alkynyl are optionally substituted by 1 or 2 —OH, $NH_2$, —NH$C_{1-3}$alkyl or —N($C_{1-3}$alkyl)$_2$ and wherein each $C_{6-10}$aryl is unsubstituted or substituted with 1, 2 or 3 —OCH$_3$; provided that when one of $R_3$ or R'$_3$ is hydrogen, then the other is not a) a $C_{1-2}$alkyl optionally substituted with 1 or 2 —OH, —NR°R°° or mixture thereof, b) a $C_3$alkenyl optionally substituted with —OH or —NR°R°°, or c) $C_3$alkynyl optionally substituted with —OH or —NR°R°°, wherein R° and R°° are each independently selected from the group consisting of hydrogen, $C_{1-6}$alkyl- and wherein R° and R°° together with the nitrogen to which they attach form a 1-morpholinyl group or a 4, 5, 6 or 7 membered heterocyclic ring; as a single diastereomer or a mixture of diastereomers; prodrugs and pharmaceutically acceptable salts thereof; provided that for formula II, when one of $R_3$ or R'$_3$ is —CH=CH$_2$, then $R_1$ is not CH$_3$CO—. In one aspect of the above compounds, $R_3$ and R'$_3$ are each independently hydrogen and $C_{1-6}$alkyl or $C_{7-9}$alkyl. In another aspect, $R_3$ and R'$_3$ are each independently hydrogen and $C_{10-18}$alkyl.

In one aspect of the above, R is selected from the group consisting of $C_{1-6}$alkyl, $C_{1-6}$alkoxy- and $C_{6-10}$aryl $C_{1-3}$alkoxy; $R_1$ is hydrogen or R'CO—, wherein R' is selected from the group consisting of $C_{1-6}$alkyl, $C_{6-10}$aryl and aryl$C_{1-3}$alkyl-; $R_3$ is selected from the group consisting of $C_{1-6}$alkyl and optionally substituted $C_{2-6}$alkenyl; and R'$_3$ is hydrogen. In another aspect, $R_2$ is selected from the group consisting of (CH$_3$)$_2$CHCH$_2$—, t-butyl, optionally substituted phenyl, and optionally substituted heteroaryl, R is t-butoxy, $R_1$ is CH$_3$CO—, $R_3$ is beta CH$_2$=CH— and R'$_3$ is hydrogen.

In another embodiment, there is provided a compound of the formula III or formula IV:

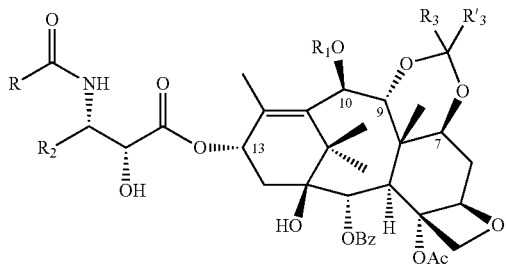

III

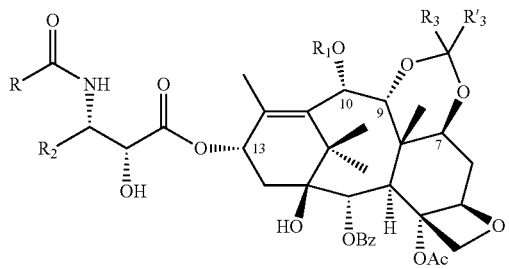

IV wherein R is selected from the group consisting of $C_{1-6}$alkyl, $C_{1-6}$alkoxy-, $C_{2-6}$alkenyl, $C_{6-10}$aryl, $C_{6-10}$aryl $C_{1-3}$alkyl and $C_{6-10}$aryl$C_{1-3}$alkoxy; $R_1$ is hydrogen or is selected from the group consisting of $C_{1-6}$alkyl, $C_{2-6}$alkenyl, R'CO—, $C_{6-10}$aryl and $C_{6-10}$aryl$C_{1-3}$alkyl, wherein R' is selected from the group consisting of $C_{1-6}$alkyl, $C_{6-10}$aryl and aryl$C_{1-3}$alkyl-; $R_2$ is selected from the group consisting of optionally substituted $C_{1-6}$alkyl, optionally substituted phenyl and optionally substituted heteroaryl; $R_3$ is hydrogen or is selected from the group consisting of $C_{1-18}$alkyl, $C_{2-6}$alkenyl, $C_{2-6}$alkynyl, $C_{6-10}$aryl and $C_{6-10}$aryl$C_{1-3}$alkyl, wherein each $C_{1-18}$alkyl, $C_{3-6}$alkenyl and $C_{3-6}$alkynyl are optionally substituted by 1 or 2 —OH, $NH_2$, —NH$C_{1-3}$alkyl or —N($C_{1-3}$alkyl)$_2$ and wherein each $C_{6-10}$aryl is unsubstituted or substituted with 1, 2 or 3 —OCH$_3$; R'$_3$ is hydrogen or is selected from the group consisting of $C_{1-18}$alkyl, $C_{2-6}$alkenyl, $C_{2-6}$alkynyl, $C_{6-10}$aryl and $C_{6-10}$aryl$C_{1-3}$alkyl, wherein each $C_{1-18}$alkyl, $C_{3-6}$alkenyl and $C_{3-6}$alkynyl are optionally substituted by 1 or 2 —OH, $NH_2$, —NH$C_{1-3}$alkyl or —N($C_{1-3}$alkyl)$_2$ and wherein each $C_{6-10}$aryl is unsubstituted or substituted with 1, 2 or 3 —OCH$_3$; provided that when one of $R_3$ or R'$_3$ is hydrogen, then the other is not a) a $C_{1-2}$alkyl optionally substituted with 1 or 2 —OH, —NR°R°° or mixture thereof, b) a $C_3$alkenyl optionally substituted with —OH or —NR°R°°, or c) $C_3$alkynyl optionally substituted with —OH or —NR°R°°, wherein R° and R°° are each independently selected from the group consisting of hydrogen, $C_{1-6}$alkyl- and wherein R° and R°° together with the nitrogen to which they attach form a 1-morpholinyl group or a 4, 5, 6 or 7 membered heterocyclic ring; as a single diastereomer or a mixture of diastereomers; prodrugs and pharmaceutically acceptable salts thereof; provided that for formula IV, when one of $R_3$ or R'$_3$ is —CH=CH$_2$, then $R_1$ is not CH$_3$CO—. In one aspect of the above compound, R is selected from the group consisting of $C_{1-6}$alkyl, $C_{1-6}$alkoxy- and $C_{6-10}$aryl $C_{1-3}$alkoxy; $R_1$ is hydrogen or R'CO—, wherein R' is selected from the group consisting of $C_{1-6}$alkyl, $C_{6-10}$aryl and aryl$C_{1-3}$alkyl-; $R_3$ is selected from the group consisting of $C_{1-6}$alkyl and optionally substituted $C_{2-6}$alkenyl; and R'$_3$ is hydrogen. In another aspect of the above, $R_2$ is selected from the group consisting of (CH$_3$)$_2$CHCH$_2$—, t-butyl, optionally substituted phenyl and optionally substituted heteroaryl, R is tert-butoxy, $R_1$ is CH$_3$CO—, $R_3$ is beta CH$_2$=CH— and R'$_3$ is hydrogen. In one aspect of the above compounds, $R_3$ and R'$_3$ are each independently hydrogen and $C_{1-6}$alkyl or $C_{7-9}$alkyl. In another aspect, $R_3$ and R'$_3$ are each independently hydrogen and $C_{10-18}$alkyl. In another aspect of the above, R'$_3$ is hydrogen and the stereochemistry of $R_3$ at the 7,9-bridge ring is selected from the group consisting of:

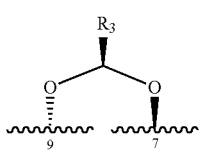

(beta configuration) and

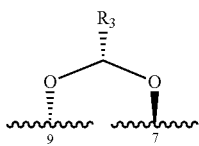

(alpha configuration), or a mixture of the alpha and beta isomers. In another aspect of the above, the stereochemistry of $R_3$ at the 7,9-bridge ring is:

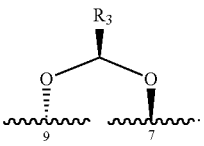

In another aspect of each of the above compounds, after isolation using the chromatographic methods described herein, the compound is greater than 95% pure, greater than 97% pure or greater than 99% pure.

In another embodiment, there is provided a pharmaceutical composition comprising: a) a therapeutically effective amount of a compound of each of the above compounds, in the form of a single diastereoisomer; and b) at least one pharmaceutically acceptable excipient, diluent or adjuvant. In another aspect, the composition further comprises temozolomide and/or Avastin. In another aspect, the above compositions further comprise one or more therapeutic agent selected from the group consisting of aromatase inhibitors, antiestrogen, anti-androgen, a gonadorelin agonists, topoisomerase 1 inhibitors, topoisomerase 2 inhibitors, microtubule active agents, alkylating agents, anthracyclines, corticosteroids, IMiDs, protease inhibitors, IGF-1 inhibitors, CD40 antibodies, Smac mimetics, FGF3 modulators, mTOR inhibitors, HDAC inhibitors, IKK inhibitors, P38MAPK inhibitors, HSP90 inhibitors, akt inhibitors, antineoplastic agents, antimetabolites, platin containing compounds, lipid- or protein kinase-targeting agents, protein- or lipid phosphatase-targeting agents, anti-angiogentic agents, agents that induce cell differentiation, bradykinin 1 receptor antagonists, angiotensin II antagonists, cyclooxygenase inhibitors, heparanase inhibitors, lymphokine inhibitors, cytokine inhibitors, bisphosphanates, rapamycin derivatives, anti-apoptotic pathway inhibitors, apoptotic pathway agonists, PPAR agonists, inhibitors of Ras isoforms, telomerase inhibitors, protease inhibitors, metalloproteinase inhibitors and aminopeptidase inhibitors, cytostatic agent, cytotoxic agent, taxane, topoisomerase II inhibitor, topoisomerase I inhibitor, tubulin interacting agent, antibodies, antiangiogenics, COX-2 inhibitors, hormonal agent, thymidilate synthase inhibitor, anti-metabolite, alkylating agent, farnesyl protein transferase inhibitor, signal transduction inhibitor, EGFR kinase inhibitor, antibody to EGFR, C-abl kinase inhibitor, hormonal therapy combination and aromatase combination.

In another embodiment, there is provided a method for the treatment of cancer in a patient comprising administering to the patient a therapeutically effective amount of a compound or composition of each of the above to a patient in need of such treatment. In one aspect of the method, the cancer is selected from the group consisting of leukemia, neuroblastoma, glioblastoma, cervical, colorectal, pancreatic, renal and melanoma. In another aspect, the cancer is selected from the group consisting of lung, breast, prostate, ovarian and head and neck. In one aspect, the cancer is colorectal cancer. In another aspect, the cancer is pancreatic cancer. In another aspect, the cancer is neuroblastoma or a glioblastoma.

In one aspect of the above methods, the compound is administered simultaneously, separately or sequentially with a chemotherapeutical agent selected from temozolomide, cisplatin, 5-flurouracil, taxotere or gemcitabine, preferably temozolomide. In another aspect, the compound is administered simultaneously, separately or sequentially with temozolomide. In another aspect of the above, the methods further comprise administering radiation therapy. In another aspect, the method is used in combination with surgical removal of a cancer. In another aspect, the composition is administered simultaneously separately or sequentially with aromatase inhibitors, antiestrogen, anti-androgen, a gonadorelin agonists, topoisomerase 1 inhibitors, topoisomerase 2 inhibitors, microtubule active agents, alkylating agents, anthracyclines, corticosteroids, IMiDs, protease inhibitors, IGF-1 inhibitors, CD40 antibodies, Smac mimetics, FGF3 modulators, mTOR inhibitors, HDAC inhibitors, IKK inhibitors, P38MAPK inhibitors, HSP90 inhibitors, akt inhibitors, antineoplastic agents, antimetabolites, platin containing compounds, lipid- or protein kinase-targeting agents, protein- or lipid phosphatase-targeting agents, anti-angiogentic agents, agents that induce cell differentiation, bradykinin 1 receptor antagonists, angiotensin II antagonists, cyclooxygenase inhibitors, heparanase inhibitors, lymphokine inhibitors, cytokine inhibitors, bisphosphanates, rapamycin derivatives, anti-apoptotic pathway inhibitors, apoptotic pathway agonists, PPAR agonists, inhibitors of Ras isoforms, telomerase inhibitors, protease inhibitors, metalloproteinase inhibitors and aminopeptidase inhibitors, cytostatic agent, cytotoxic agent, taxane, topoisomerase II inhibitor, topoisomerase I inhibitor, tubulin interacting agent, antibodies, antiangiogenics, COX-2 inhibitors, hormonal agent, thymidilate synthase inhibitor, anti-metabolite, alkylating agent, farnesyl protein transferase inhibitor, signal transduction inhibitor, EGFR kinase inhibitor, antibody to EGFR, C-abl kinase inhibitor, hormonal therapy combination and aromatase combination.

In another embodiment, there is provided a pharmaceutical composition for oral administration comprising: a) a therapeutically effective amount of a compound as described above in the form of a single diastereoisomer; and b) at least one pharmaceutically acceptable excipient, diluent or adjuvant. In one aspect, the composition further comprises temozolomide and/or Avastin. In another aspect, the composition further comprise one or more therapeutic agents selected from the group consisting of aromatase inhibitors, antiestrogen, anti-androgen, a gonadorelin agonists, topoisomerase 1 inhibitors, topoisomerase 2 inhibitors, microtubule active agents, alkylating agents, anthracyclines, corticosteroids, IMiDs, protease inhibitors, IGF-1 inhibitors, CD40 antibodies, Smac mimetics, FGF3 modulators, mTOR inhibitors, HDAC inhibitors, IKK inhibitors, P38MAPK inhibitors, HSP90 inhibitors, akt inhibitors, antineoplastic agents, antimetabolites, platin containing compounds, lipid- or protein kinase-targeting agents, protein- or lipid phosphatase-targeting agents, anti-angiogentic agents, agents that induce cell differentiation, bradykinin 1 receptor antagonists, angiotensin II antagonists, cyclooxygenase inhibitors, heparanase inhibitors, lymphokine inhibitors, cytokine inhibitors, bisphosphanates, rapamycin derivatives, anti-apoptotic pathway inhibitors, apoptotic pathway agonists, PPAR agonists, inhibitors of Ras isoforms, telomerase inhibitors, protease inhibitors, metalloproteinase inhibitors and aminopeptidase inhibitors, cytostatic agent, cytotoxic agent, taxane, topoisomerase II inhibitor, topoisomerase I inhibitor, tubulin interacting agent, antibodies, antiangiogenics, COX-2 inhibitors, hormonal agent, thymidilate synthase inhibitor, anti-metabolite, alkylating agent, farnesyl protein transferase inhibitor, signal transduction inhibitor, EGFR kinase inhibitor, antibody to EGFR, C-abl kinase inhibitor, hormonal therapy combination and aromatase combination.

In another embodiment, there is provided a method for the treatment of cancer in a patient comprising oral administration to the patient of a therapeutically effective amount of a compound as described above to a patient in need of such treatment. In one aspect of the above method, the cancer is selected from the group consisting of leukemia, neuroblastoma, glioblastoma, cervical, colorectal, pancreatic, renal and melanoma. In another aspect of the method, the cancer is selected from the group consisting of lung, breast, prostate, ovarian and head and neck. In another aspect, the cancer is colorectal cancer, pancreatic cancer, neuroblastoma or a glioblastoma. In another aspect of the above method, the compound is administered simultaneously, separately or sequentially with a chemotherapeutical agent selected from temozolomide, cisplatin, 5-flurouracil, taxotere or gemcitabine, preferably temozolomide. In another aspect of the above method, the compound is administered simultaneously, separately or sequentially temozolomide. In another aspect of the above, the methods further comprise administering radiation therapy. In another aspect of the above, the method is used in combination with surgical removal of a cancer. In another aspect of the above methods, the composition is administered simultaneously, separately or sequentially with aromatase inhibitors, antiestrogen, anti-androgen, a gonadorelin agonists, topoisomerase 1 inhibitors, topoisomerase 2 inhibitors, microtubule active agents, alkylating agents, anthracyclines, corticosteroids, IMiDs, protease inhibitors, IGF-1 inhibitors, CD40 antibodies, Smac mimetics, FGF3 modulators, mTOR inhibitors, HDAC inhibitors, IKK inhibitors, P38MAPK inhibitors, HSP90 inhibitors, akt inhibitors, antineoplastic agents, antimetabolites, platin containing compounds, lipid- or protein kinase-targeting agents, protein- or lipid phosphatase-targeting agents, anti-angiogentic agents, agents that induce cell differentiation, bradykinin 1 receptor antagonists, angiotensin II antagonists, cyclooxygenase inhibitors, heparanase inhibitors, lymphokine inhibitors, cytokine inhibitors, bisphosphanates, rapamycin derivatives, anti-apoptotic pathway inhibitors, apoptotic pathway agonists, PPAR agonists, inhibitors of Ras isoforms, telomerase inhibitors, protease inhibitors, metalloproteinase inhibitors and aminopeptidase inhibitors, cytostatic agent, cytotoxic agent, taxane, topoisomerase II inhibitor, topoisomerase I inhibitor, tubulin interacting agent, antibodies, antiangiogenics, COX-2 inhibitors, hormonal agent, thymidilate synthase inhibitor, anti-metabolite, alkylating agent, farnesyl protein transferase inhibitor, signal transduction inhibitor, EGFR kinase inhibitor, antibody to EGFR, C-abl kinase inhibitor, hormonal therapy combination and aromatase combination.

In another embodiment, there is provided a process for the preparation of compound of formula I: (See FIG. 1)

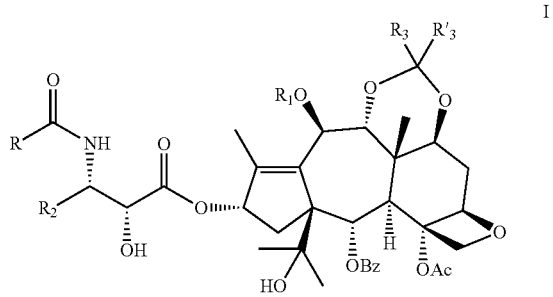

wherein: R is selected from the group consisting of $C_{1-6}$alkyl, $C_{1-6}$alkoxy-, $C_{2-6}$alkenyl, $C_{6-10}$aryl and $C_{6-10}$aryl$C_{1-3}$alkyl; $R_1$ is hydrogen or is selected from the group consisting of $C_{1-6}$alkyl, $C_{2-6}$alkenyl, R'CO—, $C_{6-10}$aryl and $C_{6-10}$aryl $C_{1-3}$alkyl, wherein R' is selected from the group consisting of $C_{1-6}$alkyl, $C_{6-10}$aryl and aryl$C_{1-3}$alkyl-; $R_2$ is selected from the group consisting of $C_{1-6}$alkyl, optionally substituted phenyl and optionally substituted heteroaryl; $R_3$ is hydrogen or is selected from the group consisting of $C_{1-18}$alkyl, $C_{2-6}$alkenyl, $C_{2-6}$alkynyl, $C_{6-10}$aryl and $C_{6-10}$aryl$C_{1-3}$alkyl, wherein each $C_{1-18}$alkyl, $C_{3-6}$alkenyl and $C_{3-6}$alkynyl are optionally substituted by 1 or 2 —OH, $NH_2$, —NH$C_{1-3}$alkyl or —N($C_{1-3}$alkyl)$_2$ and wherein each $C_{6-10}$aryl is unsubstituted or substituted with 1, 2 or 3 —OCH$_3$; $R'_3$ is hydrogen or is selected from the group consisting of $C_{1-18}$alkyl, $C_{2-6}$alkenyl, $C_{2-6}$alkynyl, $C_{6-10}$aryl and $C_{6-10}$aryl$C_{1-3}$alkyl, wherein each $C_{1-18}$alkyl, $C_{3-6}$alkenyl and $C_{3-6}$alkynyl are optionally substituted by 1 or 2 —OH, $NH_2$, —NH$C_{1-3}$alkyl or —N($C_{1-3}$alkyl)$_2$ and wherein each $C_{6-10}$aryl is unsubstituted or substituted with 1, 2 or 3 —OCH$_3$; provided that when one of $R_3$ or $R'_3$ is hydrogen, then the other is not a) a $C_{1-2}$alkyl optionally substituted with 1 or 2 —OH, —NR°R°° or mixture thereof, b) a $C_3$alkenyl optionally substituted with —OH or —NR°R°°, or c) $C_3$alkynyl optionally substituted with —OH or —NR°R°°, wherein R° and R°° are each independently selected from the group consisting of hydrogen, $C_{1-6}$alkyl- and wherein R° and R°° together with the nitrogen to which they attach form a 1-morpholinyl group or a 4, 5, 6 or 7 membered heterocyclic ring; and $P_1$ is a protecting group;

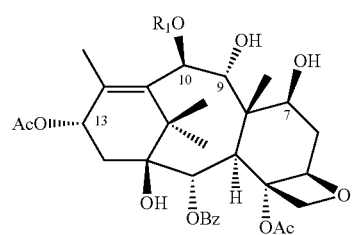

the process comprising the steps of treating a compound of the formula 5 under condition sufficient to effect a rearrangement reaction to form a compound of the formula 6;

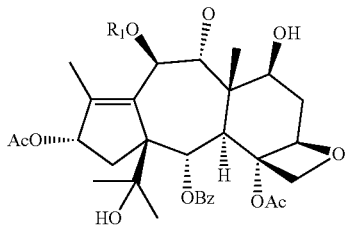

ring formation to form an acetal or ketal of the formula 7;

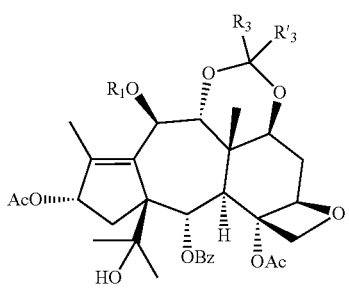

selective de-acetylation of the C-13 acetate to form a compound of the formula 8;

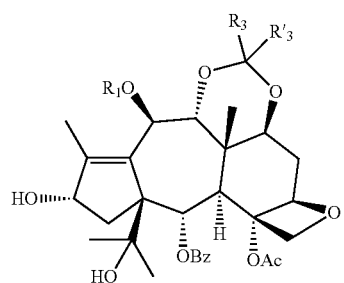

coupling of the compound of the formula 8 with a side chain of the formula 9 or 10;

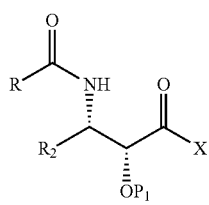

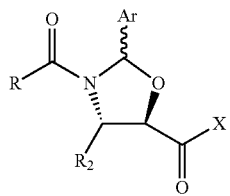

and deprotecting the protecting group $P_1$ or Ar to form the compound of the formula I. In one aspect, of the above process, the condition sufficient to effect a rearrangement reaction of the compound of the formula 5 is wet acid in an organic solvent. In another aspect of the above process, the acid is selected from the group consisting of CSA, TFA, p-TsOH, Montmorillonite clay and polymer supported acidic catalysts.

The compounds described herein may be mixtures of the stereoisomers of the 7,9-bridge, for example as diastereomeric mixtures, or they may be single isomers with respect to a particular stereocenter as provided herein. The present application also provides pharmaceutical compositions comprising a diastereoisomer of the above formula, in which the diastereomer is greater than 90% pure, greater than 95% pure, greater than 97% pure or greater than 99% pure. In certain aspects of the above compounds, the purity is determined by HPLC or by isolation of the compound using novel methods described herein.

In certain embodiments, the stereochemistry of the 7,9-bridge in such compounds is:

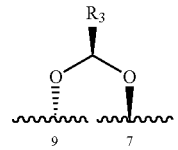

In another embodiment, the stereochemistry of the 7,9-bridge is:

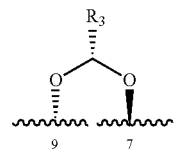

In another embodiment of each of the above compounds having the stereochemistry at the 7,9-bridge as beta, alpha or a mixture thereof, the compounds also have a stereochemistry at C-10 that is alpha, beta or mixtures thereof:

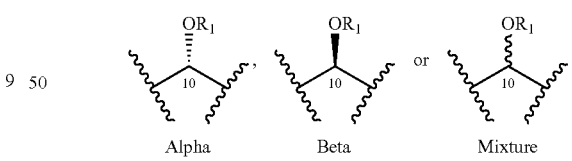

Representative processes for the preparation of the compounds of the present application are also illustrated in FIG. 6. In one embodiment, the compound of the formula V, which may be obtained from the de-acetylation of the C-13 acetate of 9-DHB (5b.1, where C-10 is beta —OAc), and placing a protecting group P on the 13 hydroxyl, may undergo a rearrangement reaction (or an isomerization reaction) to the corresponding abeo-taxane structure VI under acidic conditions. In one aspect, the —$OR_1$ group at C-10 is alpha or beta, or a mixture thereof. In another aspect, $R_1$ is hydrogen or is selected from the group consisting of $C_{1-6}$alkyl, $C_{2-6}$alkenyl, R'CO—, $C_{6-10}$aryl and $C_{6-10}$aryl$C_{1-3}$alkyl, wherein R' is selected from the group consisting of $C_{1-6}$alkyl, $C_{6-10}$aryl and arylC$_{1-3}$alkyl-. In one variation, R$_1$ is acetyl. The acidic condition may include a sulfonic acid, such as camphorsulfonic acid (CSA), p-toluene sulfonic acid (p-TsOH), trifluoroacetic acid (TFA) or an organic acid such as acetic acid, or mixtures thereof, in a protic solvent such as methanol, ethanol, propanol, isopropanol and mixtures thereof. Alternatively, the solvent may be a water wet aprotic solvent such as dichloromethane (DCM), toluene, MTBE or mixtures thereof. The water wet aprotic solvent may be a water saturated solvent. Depending on the acid, solvent or solvent mixture, the reaction may be conducted at about 20-25° C., 25-35° C. or 35-55° C., or starting from about 20-25° C. and slowly heating the reaction to refluxing temperatures for a sufficient period of time for substantially complete rearrangement to VI. The rearrangement reaction results in the abeo-taxane that retains the stereochemistry of the taxane (or baccatin) starting material, such as at C-7, C-9, C-10 and C-13 etc. For example, starting with the baccatin structure of the formula V wherein C-10 is beta, the resulting rearranged compound of formula VI will also have the chiral center where C-10 beta.

The coupling reaction at the C-13 hydroxy group of VI with a protected side chain (see FIG. 6, compounds 9 or 10a to 10f) may be performed as an acylation reaction using an activated acid known in the art, such as using acid halides, anhydrides, mixed anhydrides, beta lactams and an activated acid (e.g., using DCC/DMAP), or acid catalyzed esterification reactions using an acid such as HCl, H$_2$SO$_4$, CSA, p-TSOH, polymeric sulfonic acids etc., in a protic or aprotic organic solvent, to form VII. In one aspect, the coupling or acylating agent is 9 RCONHCHR$_2$CH(OP$_1$)C(O)X, wherein R is selected from the group consisting of C$_{1-6}$alkyl, C$_{2-6}$alkenyl, R'O—, C$_{6-10}$aryl, C$_{6-10}$arylC$_{1-3}$alkyl and C$_{6-10}$arylC$_{1-3}$alkoxy, wherein R' is selected from the group consisting of C$_{1-6}$alkyl, C$_{6-10}$aryl and arylC$_{1-3}$alkyl-, R$_2$ is C$_{1-6}$alkyl, optionally substituted phenyl or optionally substituted heteroaryl, and X is selected from —OH, —OCOC$_{1-6}$alkyl, —F, —Cl, —Br and —I. In another aspect, the coupling agent is 10e or 10f, wherein R is C$_{1-6}$alkyl, C$_{1-6}$alkoxy-, C$_{2-6}$alkenyl, C$_{6-10}$aryl or C$_{6-10}$arylC$_{1-3}$alkyl; R$_2$ is C$_{1-6}$alkyl, phenyl, or heteroaryl. In one aspect, Ar is phenyl, 2-methoxyphenyl, 4-methoxyphenyl, 2,6-dimethoxyphenyl or 2,4,6-trimethoxyphenyl. In one aspect of the compound VII, R is t-BuO and R$_2$ is —CH$_2$CH(CH$_3$)$_2$.

The 7,9-bridge ring formation reaction for the conversion of VII having a 7,9-diol to the corresponding 7,9-bridged compound VIII may be performed with the reaction of VII with an aldehyde, R$_3$CHO, a dialkyl acetal (R$_3$—CH(OC$_{1-4}$ alkyl)$_2$ wherein R$_3$ is selected from the group consisting of C$_{1-18}$alkyl, optionally substituted C$_{2-6}$alkenyl, C$_{2-6}$alkynyl, optionally substituted C$_{6-10}$aryl, optionally substituted heteroaryl and C$_{6-10}$arylC$_{1-3}$alkyl; or with a dialkyl ketal (R$_3$R'$_3$C(OC$_{1-4}$ alkyl)$_2$), wherein R$_3$ is selected from the group consisting of C$_{1-18}$alkyl, optionally substituted C$_{2-6}$alkenyl, C$_{2-6}$alkynyl, optionally substituted C$_{6-10}$aryl, optionally substituted heteroaryl and C$_{6-10}$arylC$_{1-3}$alkyl; and R'$_3$ is selected from the group consisting of optionally substituted C$_{1-18}$alkyl, C$_{2-6}$alkenyl, C$_{2-6}$alkynyl, optionally substituted C$_{6-10}$aryl, optionally substituted heteroaryl and C$_{6-10}$arylC$_{1-3}$alkyl. In one aspect of the compound VIII, R'$_3$ is hydrogen and R$_3$ is —CH═CH$_2$. In another aspect, R$_3$ is beta —CH═CH$_2$. In another aspect, R$_3$ is an optionally substituted C$_{2-6}$alkenyl. In one aspect, the 7,9-ring formation reaction may be performed in the presence of an acid, such as a sulphonic acid. The acid may be used in a catalytic amount, and the acid may be camphorsulphonic acid or p-toluenesulfonic acid. In another aspect, the acid catalysts include montmorillonite clay and polymer supported acidic catalysts.

The 7,9-ring formation may be performed in an organic solvent, such as acetonitrile, DCM (CH$_2$Cl$_2$), THF or toluene, at about room temperatures (20-25° C.).

Where the 7,9-ring formation reaction to form VIII, wherein R'$_3$ is hydrogen and the 7,9-ring is an acetal, the resulting diastereomer of the 7,9-bridge may also be obtained as a single isomer by separating mixtures of alpha and beta isomers. In one aspect, the separation may be performed using chromatography to provide the desired mixture of isomers or single isomer, such as the beta isomer of R$_3$, where R'$_3$ is hydrogen. In one aspect, chromatographic separation may be performed using silica, such as spherical silica. As provided herein, normal phase purification at differing scales were carried out on various sizes of columns packed with YMC silica (Silica gel S-30-50 μm 120 Å) or Kromasil silica (100 Å, 10 μm Kromasil silica gel) and with solvent mixtures, such as solvents prepared from n-Heptane/waIBAc (1% water and 1% acetic acid in isobutyl acetate) or n-Heptane/waMTBE (1% water and 1% acetic acid in Methyl-t-butyl ether), that provided the single isomer (e.g., the beta isomer or the alpha isomer) in greater than 95%, 97% and greater than about 99% isomeric purity. Using the purification methods disclosed herein the specific compounds were also obtained in greater than 95%, greater than 97%, greater than 98% and greater than 99% chemical purity.

In another embodiment, the compound of the formula VIII may be prepared starting with V with the 7,9-ring formation to form IX, followed by addition of the protected side chain to form X, in turn followed by a rearrangement reaction to form VIII. Alternatively, the coupling reaction with the side chain may be performed before the rearrangement reaction to form VIII. IX may be prepared from the reaction of V with an aldehyde, R$_3$CHO, a dialkyl acetal (R$_3$—CH(OC$_{1-4}$ alkyl)$_2$ wherein R$_3$ is selected from the group consisting of C$_{1-18}$alkyl, optionally substituted C$_{2-6}$alkenyl, C$_{2-6}$alkynyl, C$_{6-10}$aryl and C$_{6-10}$arylC$_{1-3}$alkyl; or with a dialkyl ketal (R$_3$R'$_3$C(OC$_{1-4}$ alkyl)$_2$), wherein R$_3$ is selected from the group consisting of C$_{1-18}$alkyl, optionally substituted C$_{2-6}$alkenyl, C$_{2-6}$alkynyl, C$_{6-10}$aryl and C$_{6-10}$arylC$_{1-3}$alkyl; and R'$_3$ is selected from the group consisting of C$_{1-18}$alkyl, C$_{2-6}$alkenyl, C$_{2-6}$alkynyl, C$_{6-10}$aryl and C$_{6-10}$arylC$_{1-3}$alkyl. In one aspect of the compound IX, R'$_3$ is hydrogen and R$_3$ is —CH═CH$_2$. In another aspect, R$_3$ is beta —CH═CH$_2$. In another aspect, R$_3$ is an optionally substituted C$_{2-6}$alkenyl. In one aspect, the 7,9-ring formation reaction may be performed in the presence of an acid, such as a sulphonic acid. The acid may be used in a catalytic amount, and the acid may be camphorsulphonic acid or p-toluenesulfonic acid. In another aspect, the acid catalysts include montmorillonite clay and polymer supported acidic catalysts. The 7,9-ring formation may be performed in an organic solvent, such as acetonitrile, DCM (CH$_2$Cl$_2$), THF or toluene, at about room temperatures (20°-25° C.). In one aspect, the separation of the diastereomers may be performed using chromatography, as described above, to provide the desired mixture of isomers or a single isomer, such as the beta isomer of R$_3$, where R'$_3$ is hydrogen. Rearrangement of X to VIII may be performed under the same reaction conditions as described for the reaction of V to VI. In one aspect, there is provided a product obtained from the process of rearrangement of the compound of the formula X under the rearrangement conditions described above.

Alternatively, the compound of formula VIII may be prepared from the rearrangement reaction of the compound of the formula IX under the same reaction conditions as described for the reaction of V to VI followed by coupling of a protected side chain as in the conversion of compound VI to compound VII. In one aspect, there is provided a product obtained from the process of rearrangement of the compound of the formula IX under the rearrangement conditions described above followed by coupling of a protected side chain to the 13 hydroxyl to provide the compound of the formula VIII.

The compound of the formula X may be prepared by the coupling reaction of IX with a coupling agent (9 or 10a to 10f) under standard coupling conditions known in the art, or under the similar conditions as described above for the coupling reaction of VI to form VII.

Optionally, in any of the above reaction processes, depending on the reaction conditions, any unprotected reactive hydroxyl groups or amine group (such as C-7, C-9, C-10, C-13 or the nitrogen on the coupling reagent) may be protected with a hydroxyl protecting group and/or an amine protecting group. The selection of a particular hydroxyl or amine protecting group will depend on the subsequent reaction conditions and reaction sequence to provide the desired product, as disclosed herein. In one aspect, a selected protecting group may be removed after the 7,9-ring formation reaction to form VIII. In another aspect of the above compounds VII and VIII, $R_1$ is —$COCH_3$. In one aspect of the compound VIII, $R'_3$ is hydrogen, and the configuration of the 7,9-bridge is beta:

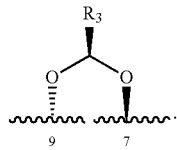

A selected single diastereomer of the compounds of FIG. 6, including the compounds of the formulae VII, IX or X may be isolated with the chromatographic separation methods of using silica, such as spherical silica, as described above. The selected single diastereomers may be obtained as a single isomer in greater than 95%, 97% and greater than about 99% isomeric purity.

The variables of the compounds defined herein and in FIGS. 1-6, unless noted otherwise, are as follows:

R is selected from the group consisting of $C_{1-6}$alkyl, $C_{1-6}$alkoxy-, $C_{2-6}$alkenyl, $C_{6-10}$aryl, $C_{6-10}$aryl$C_{1-3}$alkyl and $C_{6-10}$aryl$C_{1-3}$alkoxy;

$R_1$ is hydrogen or is selected from the group consisting of $C_{1-6}$alkyl, $C_{2-6}$alkenyl, R'CO—, $C_{6-10}$aryl and $C_{6-10}$aryl$C_{1-3}$alkyl, wherein R' is selected from the group consisting of $C_{1-6}$alkyl, $C_{6-10}$aryl and aryl$C_{1-3}$alkyl-;

$R_2$ is selected from the group consisting of $C_{1-6}$alkyl, phenyl and heteroaryl;

$R_3$ is hydrogen or is selected from the group consisting of $C_{1-18}$alkyl, optionally substituted $C_{2-6}$alkenyl, $C_{2-6}$alkynyl, $C_{6-10}$aryl and $C_{6-10}$aryl$C_{1-3}$alkyl, and wherein each $C_{6-10}$aryl is unsubstituted or substituted with 1, 2 or 3 —$OCH_3$;

$R'_3$ is hydrogen or is selected from the group consisting of $C_{1-18}$alkyl, $C_{2-6}$alkenyl, $C_{2-6}$alkynyl, $C_{6-10}$aryl and $C_{6-10}$aryl$C_{1-3}$alkyl, and wherein each $C_{6-10}$aryl is unsubstituted or substituted with 1, 2 or 3 —$OCH_3$;

Ar is phenyl, 2-methoxyphenyl, 4-methoxyphenyl, 2,6-dimethoxyphenyl or 2,4,6-trimethoxyphenyl;

$P_1$ is an alcohol protecting group selected from the group consisting of TBS, CBz, Bn, BOM, Troc, trichloroethyl, allyl, alloc, phenoxyacetate, methoxyacetate, phenylacetate, ethoxyethyl, acetyl, benzoyl, benzyl, TMS (trimethyl silyl), MEM (beta-methoxyethoxymethyl ether), DMT, MMT, PMB, methylthiomethyl ether, NDMS (2-norbornyldimethylsilyl), TES (triethylsilyl), TBDMS, THP, Trityl, Piv and MOM; and X is selected from —OH, —$OCOC_{1-6}$alkyl, —F, —Cl, —Br and —I.

DETAILED DESCRIPTION

Unless specifically noted otherwise herein, the definitions of the terms used are standard definitions used in the art of organic synthesis and pharmaceutical sciences. Exemplary embodiments, aspects and variations are illustrative in the figures and drawings, and it is intended that the embodiments, aspects and variations, and the figures and drawings disclosed herein are to be considered illustrative and not limiting.

DEFINITIONS

As used herein, the term "alkyl", alone or in combination, refers to an optionally substituted straight chain or branched chain alkyl radical having from 1 to 20 carbon atoms (e.g. $C_{1-20}$alkyl), from 1 to 10 carbon atoms or form 1 to 6 carbon atoms. Optionally, an "alkyl" group may have oxygen, nitrogen or sulfur atoms inserted between the carbon atoms in the chain or as indicated. A $C_{1-20}$alkyl, for example, includes alkyl groups that have a chain of between 1 and 20 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, penta-1,4-dienyl, hexa-1,3-dienyl, hexa-1,3,5-trienyl and the like. An alkyl group may also be represented, for example, as a —$(CR_1R_2)_m$— group where $R_1$ and $R_2$ are independently hydrogen or are independently absent, and for example, m is 1 to 8, and such representation is also intended to cover both saturated and unsaturated alkyl groups. Lower alkyl groups include groups of 1, 2, 3, 4, 5, 6, 7 or 8 carbon atoms (i.e., $C_{1-4}$alkyl or $C_{1-8}$alkyl etc.,) and can be straight or branched and can optionally be substituted with one or more cyclic moieties of 3, 4, 5, 6, 7 or 8 carbon atoms. Examples of lower alkyl groups include methyl, ethyl, n-propyl, isopropyl, n-butyl, sec-butyl, isobutyl, t-butyl, pentyl, neopentyl, hexyl, heptyl and octyl. Examples of cyclic groups include cyclopropyl, cyclobutylmethyl, cyclopentyl, cyclohexyl, cycloheptyl, cyclooctyl etc. In an embodiment, lower alkyl groups are straight or branched alkyl groups of up to 6 carbon atoms.

An alkyl as noted with another group such as an aryl group, represented as "arylalkyl" for example, is intended to be a straight, branched, saturated or unsaturated aliphatic divalent group with the number of atoms indicated in the alkyl group (as in $C_{1-20}$alkyl, for example) and/or aryl group (as in $C_{5-14}$aryl, for example) or when no atoms are indicated means a bond between the aryl and the alkyl group. Nonexclusive examples of such group include benzyl, phenethyl and the like.

An "alkylene" or "alkylenyl" group is a straight, branched, saturated or unsaturated aliphatic divalent group with the number of atoms indicated in the alkyl group; for example, a —$C_{1-3}$alkylene- or —$C_{1-3}$alkylenyl-.

The term "alkenyl", alone or in combination, refers to an optionally substituted straight-chain or branched-chain hydrocarbon radical having one or more carbon-carbon double-bonds and having from 2 to about 18 carbon atoms. Examples of alkenyl radicals include ethenyl, propenyl, 1,4-butadienyl and the like. Lower alkenyl groups include groups having 2, 3, 4, 5, 6, 7 or 8 carbon atoms and can be straight or branched and can optionally be substituted with one or more cyclic moieties of 3, 4, 5, 6, 7 or 8 carbon atoms. Examples of lower alkenyl groups include ethenyl, propenyl, butenyl, pentenyl, hexenyl, heptenyl, octenyl and examples of cyclic moieties include cyclohexenylmethyl, cyclopentenyl, cyclohexenyl, cycloheptenyl, cyclooctenyl and the like.

The term "alkoxy" refers to an alkyl ether radical wherein the term alkyl is defined as above. Examples of alkoxy radicals include methoxy, ethoxy, n-propoxy, isopropoxy, n-butoxy, iso-butoxy, sec-butoxy, tert-butoxy and the like. The term "lower alkoxy" is an oxygen atom substituted by a lower alkyl group. In one aspect, a lower alkoxy group is the tert-butyloxy group.

The term "aryl", alone or in combination, refers to an optionally substituted aromatic ring. The term aryl includes monocyclic aromatic rings, polyaromatic rings and polycyclic ring systems. The polyaromatic and polycyclic rings systems may contain from two to four, more preferably two to three, and most preferably two rings. Examples of aryl groups include six-membered aromatic ring systems, including, without limitation, phenyl, biphenyl, naphthyl and anthryl ring systems. The aryl groups of the present application generally contain from five to six carbon atoms.

A "cyclyl" such as a monocyclyl or polycyclyl group includes monocyclic, or linearly fused, angularly fused or bridged polycycloalkyl, or combinations thereof. Such cyclyl group is intended to include the heterocyclyl analogs. A cyclyl group may be saturated, partially saturated or aromatic.

The term "diastereoisomer" refers to any group of four or more isomers occurring in compounds containing two or more asymmetric carbon atoms. Compounds that are stereoisomers of one another, but are not enantiomers are called diastereosiomers.

"Halogen" or "halo" means fluorine, chlorine, bromine or iodine.

A "heterocyclyl" or "heterocycle" is a cycloalkyl wherein one or more of the atoms forming the ring is a heteroatom that is a N, O or S. Non-exclusive examples of heterocyclyl include piperidyl, 4-morpholyl, 4-piperazinyl, pyrrolidinyl, 1,4-diazaperhydroepinyl, 1,3-dioxanyl, and the like.

"Heteroaryl" means a cyclic aromatic group with at least five or six ring atoms, wherein at least one ring atom is a heteroatom and the remaining are carbon atoms. Heteroaryl groups may include, for example, furan, imidazole, isoxazole, oxazole, pyrazine, pyridine, pyrimidine, triazole and tetrazole. Heteroaryl also includes, for example, bicyclic or tricyclic heteroaryl rings. These bicyclic or tricyclic heteroaryl rings include benzo[b]furan, benzimidazole, quinazoline, quinoline, isoquinoline, naphthyridine, quinolizine, indole, indazole, benzoxazole, benzopyrazole and indolizine. The bicyclic or tricyclic heteroaryl rings can be attached (or substituted) to a particular group or compound through either the heteroaryl group itself or the aryl, cycloalkyl, cycloalkenyl or heterocycloalkyl group to which it is fused. The heteroaryl groups can be substituted or unsubstituted.

The groups, substituents or functional groups described in the present application, including for example, $C_{1-10}$alkyl, alkoxy, alkenyl, aryl, heteroaryl and the like, may be unsubstituted or may be further substituted by one or two substituents. The specific substituents may include, for example, amino, halo (bromo, chloro, fluoro and iodo), oxo, hydroxyl, nitro, $C_{1-10}$alkyl, $C_{1-10}$alkoxy, $C_{1-10}$alkylCO— and the like.

The term "baccatin" or "baccatin derivatives" means the taxane derivatives in which the side chain at the 13-position of the taxane skeleton is a hydroxy group and these derivatives are often referred to in the literature as a baccatin or "baccatin I-VII" or the like depending, on the nature of the substituents on the tricyclic rings of the taxane skeleton.

The terms "taxanes," "taxane derivatives," and "taxane analogs" etc., are used interchangeably to mean compounds relating to a class of antitumor agents derived directly or semi-synthetically from *Taxus brevifolia*, the Pacific yew. Examples of such taxanes include paclitaxel and docetaxel and their natural as well as their synthetic or semi-synthetic derivatives.

The term "abeo-taxane(s)" or "abeo-taxane analog(s)" etc., are used interchangeably to mean compounds that are directly or indirectly derived from the taxanes, and having an 5-membered (pentacylic) A-ring. Such abeo-taxane may be synthetic derivatives or semi-synthetic derivatives of the taxanes or other abeo-taxanes. Representative abeo-taxanes having the particular ring structures that are distinct from the taxanes ring structures are disclosed herein.

An "alpha" or "α" designation for a substituent on a molecular structure means that the substituent is attached below the plane of the paper, or shown as a dashed line.

A "beta" or "β" designation for a substituent on a molecular structure means that the substituent is attached above the plane of the paper, or shown as a wedge line.

Where a chiral center, such as a chiral carbon, is illustrated as a straight line (bond) that is neither a dashed line nor a wedge line, the chiral center represents 1) a racemic center having a mixture of both diastereomers, 2) a single alpha stereoisomer or 3) a single alpha stereoisomer. In the absence of a designation, the structure shown with a straight line is intended to cover all three permutations. An example of such a straight line designation is illustrated in FIG. 6, at C-10 bearing the —OR$_1$ group of formula V, and compounds prepared from V. Similarly, where the bond is represented by line that is a wiggly line $\sim\sim\sim$, the line designates that the compound has a mixture of both alpha and beta stereoisomers.

"Pharmaceutically acceptable excipient" or "pharmaceutically acceptable salts" as used herein, means the excipient or salts of the compounds disclosed herein, that are pharmaceutically acceptable and provides the desired pharmacological activity. These excipients and salts include acid addition salts formed with inorganic acids such as hydrochloric acid, hydrobromic acid, phosphoric acid and the like. The salt may also be formed with organic acids such as acetic acid, propionic acid, hexanoic acid, glycolic acid, lactic acid, succinic acid, malic acid, citric acid, benzoic acid and the like.

The phrase "protecting group" as used herein means temporary substituents which protect a potentially reactive functional group from undesired chemical transformations. In some aspects, the protecting group may be part of the compound of the present application. Examples of such protecting groups include esters of carboxylic acids, silyl ethers of alcohols, and acetals and ketals of aldehydes and ketones, respectively. Representative protecting groups and their applications are provided in Greene, T. W.; Wuts, P. G. M. Protective Groups in Organic Synthesis, 4$^{th}$ ed.; Wiley: New York, 2007. Specific hydroxyl protecting groups that may be employed in the compound disclosed in the present application include TBS, CBz, Bn, BOM, PMB, Troc, trichloroethyl, allyl, alloc, phenoxyacetate, methoxyacetate, phenylacetate, ethoxyethyl, butoxyethyl THP other cyclic and acyclic acetals and ortho esters. Exemplary silyl groups for protection of hydroxyl groups include TBDMS (tert-butyldimethylsilyl), NDMS (2-norbornyldimethylsilyl), TMS (trimethylsilyl) and TES (triethylsilyl). Exemplary NH-protecting groups include benzyloxycarbonyl, t-butoxycarbonyl and triphenylmethyl. Because of the sensitive nature of certain compounds and certain protecting groups toward hydrolysis or toward particular reaction conditions, the judicious selection of the particular protecting group that may be used in any particular compound for any particular reaction process or processing steps is required. Additional, representative hydroxyl protecting groups also include acetyl, tert-butyl, benzoyl, benzyl, benzyloxymethyl, tetrahydropyranyl, 1-ethoxyethyl, allyl, formyl and the like.

"Substituted or unsubstituted" or "optionally substituted" means that a group such as, for example, alkyl, aryl, heterocyclyl, ($C_{1-8}$)cycloalkyl, hetrocyclyl($C_{1-8}$)alkyl, aryl($C_{1-8}$)alkyl, heteroaryl, heteroaryl($C_{1-8}$)alkyl, and the like, unless specifically noted otherwise, may be unsubstituted or, may substituted by 1, 2 or 3 substituents selected from the group such as halo, nitro, trifluoromethyl, trifluoromethoxy, methoxy, carboxy, —$NH_2$, —OH, —SH, —$NHCH_3$, —$N(CH_3)_2$, —SMe, —CN and the like.

"Therapeutically effective amount" means a drug amount that elicits any of the biological effects listed in the specification.

The term "7,9-bridge" as used herein with respect to the taxane ring structure, refers to the carbon atoms at position 7- and position 9-, along with the representative stereochemistry as designated at position 7 and position 9, that forms an acetal or ketal, such as a 6-membered acetal or ketal ring as depicted in the "Taxane Ring Structure" in the figure below. Similarly, for the convenience of nomenclature for discussions and for comparison purposes between the taxane ring structure and the abeo ring structure depicted in the figure below, recognizing that the Abeo-Taxane Ring has a different IUPAC numbering of the ring carbon atoms, the "corresponding" ring carbon atoms at the same position in the "Abeo-Taxane Ring Structure" are also referred to as being the carbon atoms at position 7- and position 9- that also form a 6-membered acetal (where one of $R_3$ or $R'_3$ is a hydrogen) or ketal ring (where both $R_3$ and $R'_3$ are not hydrogen. Similarly, the position carbon number 10 that is substituted with an acetate group, and the position carbon number 13 that bears a hydroxy group (that may be linked with the side chain) are referred to the same positions (i.e. carbon 10 or carbon 13) in the taxane ring structure and the abeo ring structure.

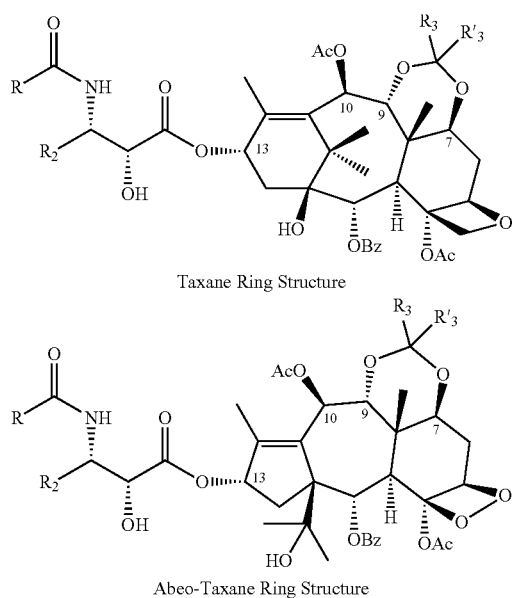

The term "abeo-taxane" means a taxane derivative in which the baccatin ring portion of the taxane has been rearranged such that a new multi-ring structure is produced—the abeo-taxane ring structure as depicted above. The representative taxane ring structure and the abeo-taxane ring structure shown above have both the 7,9-bridge ring and the C-13 acylated side chain. In this application a particular abeo-taxane ring structure is the basis of the new taxane analogs—the 11(15--->1) abeo-taxane ring structure.

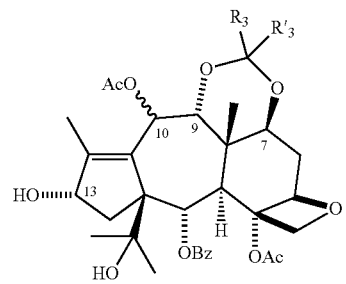

Structure of 11(15--->1) abeo-taxane without a side chain at position C-13.

Also included in the above embodiments, aspects and variations are prodrugs and their salts such as prodrugs of amino acids such as arginate and the like, gluconate, and galacturonate. Some of the compounds of the invention may form inner salts or Zwitterions. Certain of the compounds of the present invention can exist in unsolvated forms as well as solvated forms, including hydrated forms, and are intended to be within the scope of the present invention. Certain of the above compounds may also exist in one or more solid or crystalline phases or polymorphs, the variable biological activities of such polymorphs or mixtures of such polymorphs are also included in the scope of this invention. Also provided are pharmaceutical compositions comprising pharmaceutically acceptable excipients and a therapeutically effective amount of at least one compound of this application.

Pharmaceutical compositions of the compounds of this application, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride, or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols or water. Solid carriers include starch, lactose, calcium sulfate, dihydrate, terra alba, magnesium stearate or stearic acid, talc, pectin, acacia, agar, or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing, and filling for hard gelatin capsule forms. When a liquid carrier is used, the preparation will be in the form of a syrup, elixir, emulsion, or an aqueous or non-aqueous suspension. Such a liquid formulation may be administered directly p.o. or filled into a soft gelatin capsule. Suitable formulations for each of these methods of administration may be found in, for example, *Remington: The Science and Practice of Pharmacy*, A. Gennaro, ed., 20th edition, Lippincott, Williams & Wilkins, Philadelphia, Pa.

In one variation, there is provided the above compound, or a pharmaceutically acceptable salt thereof, optionally in the form of a single stereoisomer or mixture of stereoisomers thereof.

The present invention describes compounds which have an affinity to bind with tubulin and are potential drugs in the treatment of cancer and other disease conditions related to dysfunction of proteins associated with tubulin such as tau, MAP1, MAP2 and MAP4. The compounds of the present invention may be useful in the treatment of diseases when used alone or in combination with other therapies. For example, when used for the treatment of cancer, the compounds of the invention may be administered alone or in combination with radiotherapy, surgical removal, hormonal agents, antibodies, antiangiogenics, COX-2 inhibitors, and/or other chemotherapeutic agents such as taxanes, temozolomide, cisplatin, 5-fluorouracil, taxotere, gemcitabine, topoisomerase II inhibitor, topoisomerase I inhibitor, tubulin interacting agent, antibodies, antiangiogenics, COX-2 inhibitors, hormonal agent, thymidilate synthase inhibitor, anti-metabolite, alkylating agent, farnesyl protein transferase inhibitor, signal transduction inhibitor, EGFR kinase inhibitor, antibody to VEGFR, C-abl kinase inhibitor, hormonal therapy combination and aromatase combination.

The compounds of the present application may be useful in the treatment of diseases when used alone or in combination with other chemotherapeutics. For example, when used for the treatment of cancer, the compounds of the invention may be administered alone or in combination with aromatase inhibitors, antiestrogen, anti-androgen, a gonadorelin agonists, topoisomerase 1 inhibitors, topoisomerase 2 inhibitors, microtubule active agents, alkylating agents, anthracyclines, corticosteroids, IMiDs, protease inhibitors, IGF-1 inhibitors, CD40 antibodies, Smac mimetics, FGF3 modulators, mTOR inhibitors, HDAC inhibitors, IKK inhibitors, P38MAPK inhibitors, HSP90 inhibitors, akt inhibitors, antineoplastic agents, antimetabolites, platinum containing compounds, lipid- or protein kinase-targeting agents, protein- or lipid phosphatase-targeting agents, anti-angiogentic agents, agents that induce cell differentiation, bradykinin 1 receptor antagonists, angiotensin II antagonists, cyclooxygenase inhibitors, heparanase inhibitors, lymphokine inhibitors, cytokine inhibitors, bisphosphanates, rapamycin derivatives, anti-apoptotic pathway inhibitors, apoptotic pathway agonists, PPAR agonists, inhibitors of Ras isoforms, telomerase inhibitors, protease inhibitors, metalloproteinase inhibitors, aminopeptidase inhibitors, thymidilate synthase inhibitors, a DNA cross linking agents, topoisomerase I or II inhibitors, DNA alkylating agents, ribonuclease reductase inhibitors, cytotoxic factors, and growth factor inhibitors.

The compounds of the present application may be useful in the treatment of diseases when used alone or in combination with other chemotherapeutics. For example, when used for the treatment of cancer, the compounds of the invention may be administered alone or in combination with one or more pharmaceutically acceptable, inert or physiologically active diluents, adjuvants or chemotherapeutic agents selected from the group consisting of phomopsin, dolastatin, Avastin, steganacin, paclitaxel, taxotere, vinblastine, vincristine, vindesine, vinorelbine, navelbine, colchicine, maytansine, ansamitocin, Iressa, Tarceva, Herceptin, lapatinib, vandetanib, Sorafenib, BAY-57-9006, bevacizumab, cetuximab, gemtuzumab, panitumumab, rituximab, tositumomab, trastuzumab, apolizumab, oregovomab, mitumomab, alembuzumab, ibritumomab, vitaxin, SU-6668, semaxanib, sunitinib malate, SU-14813, vandetanib, Recentin, CP-547632, CEP-7055, AG-013736, pazopanib, combretastatin, squalamine, combrestatin A4 phosphate, TNP-470, neovastat, dasatinib, imatinib, nilotinib, sorafenib, sunitinib, triethylenethiophosphoramine, alitretinoin, altretamine, arsenic trioxide, asparaginase, bexarotene, denileukin diftitox, hydroxycarbamide, masoprocol, mitotane, pegaspargase, tretinoin, raltitrexed, IL-10, IL-12, bortezomib, leuprolide, interferon β, pegylated interferons, atrasentan, melphalan, cyclophosphamide, chlormethine, chlorambucil, trofosfamide, ifosfamide, nitromin, busulfan, thiotepa, chlorambucil, CC-1065, temozolomide, pipobroman, dacarbazine, mechlorethamine, procarbazine, uramustine, RSU-1069, CB-1954, hexamethylmelamine, cisplatin, carboplatin, oxaliplatin, BBR3464, satraplatin, tetraplatin, iproplatin, amsacrine, netropsin, pibenzimol, mitomycin, duocarmycin, dactinomycin, distamycin, mithramycin, chromomycin, olivomycin, anthramycin, bleomycin, liblomycin, rifamycin, actinomycin, adramycin, trichostatin A, propamidine, stilbamidine, rhizoxin, nitroacridine, geldamycin, 17-AAG, 17-DMAG, plicamycin, deoxycoformycin, levamisole, daunorubicin, doxorubicin, epirubicin, idarubicin, mitroxantrone, valrubicin, carmustine, fotemustine, lomustine, streptozocin, gemcitabine, 5-fluorouracil (5-FU), fludarabine, cytarabine, capecitabine, mercaptopurine, cladribine, clofarabine, thioguanine, pentostatin, floxuridine, pentostatin, aminopterin, methotrexate, pemetrexed, camptothecin, irinotecan, topotecan, epipodophyllotoxin, etoposide, teniposide, aminogluthetimide, anastrozole, exemestane formestane, letrozole, fadrozole, aminoglutethimide, leuprorelin, buserelin, goserelin, triptorelin, abarelix, estramustine, megestrol, flutamide, casodex, anandron, cyproterone acetate, finasteride, bicalutamide, tamoxifen or its citrate salt, droloxifene, trioxifene, raloxifene or zindoxifene, a derivative of 17-β-estradiol such as ICI 164, ICI 384, ICI 182, ICI 780, testolactone, fulvestrant, toremifene, testosterone, fluoxymesterone, dexamethasone, triamcinolone, dromostanolone propionate, megestrol acetate, methyltestosterone, chlorotrianisene, hydroxyprogesterone, medroxyprogesterone acetate, reloxafine, etanercept, thalidomide, revimid (CC-5013), aziridoquinones, misonidazole, NLA-1, RB-6145, misonidazole, nimorazole, RSU-1069, SR-4233, porfimer, photofrin, verteporfin, merocyanin 540, tin etiopurpurin, PUVA, aminolevulinic acid, methyl aminolevulinate, minodronate, zoledronic acid, ibandronate sodium hydrate or clodronate disodium, misonidazole, misonidazole, amifostene, oblimersen, TIMP-1 or TIMP-2, marimastat, TLK-286 and mixtures thereof.

In addition to the exemplary embodiments, aspects and variations described above, further embodiments, aspects and variations will become apparent by reference to the drawings and figures and by examination of the following descriptions.

EXPERIMENTAL

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989.

In some cases, protective groups may be introduced and finally removed. Suitable protective groups for amino, hydroxy and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

Example 1

Figure 2:
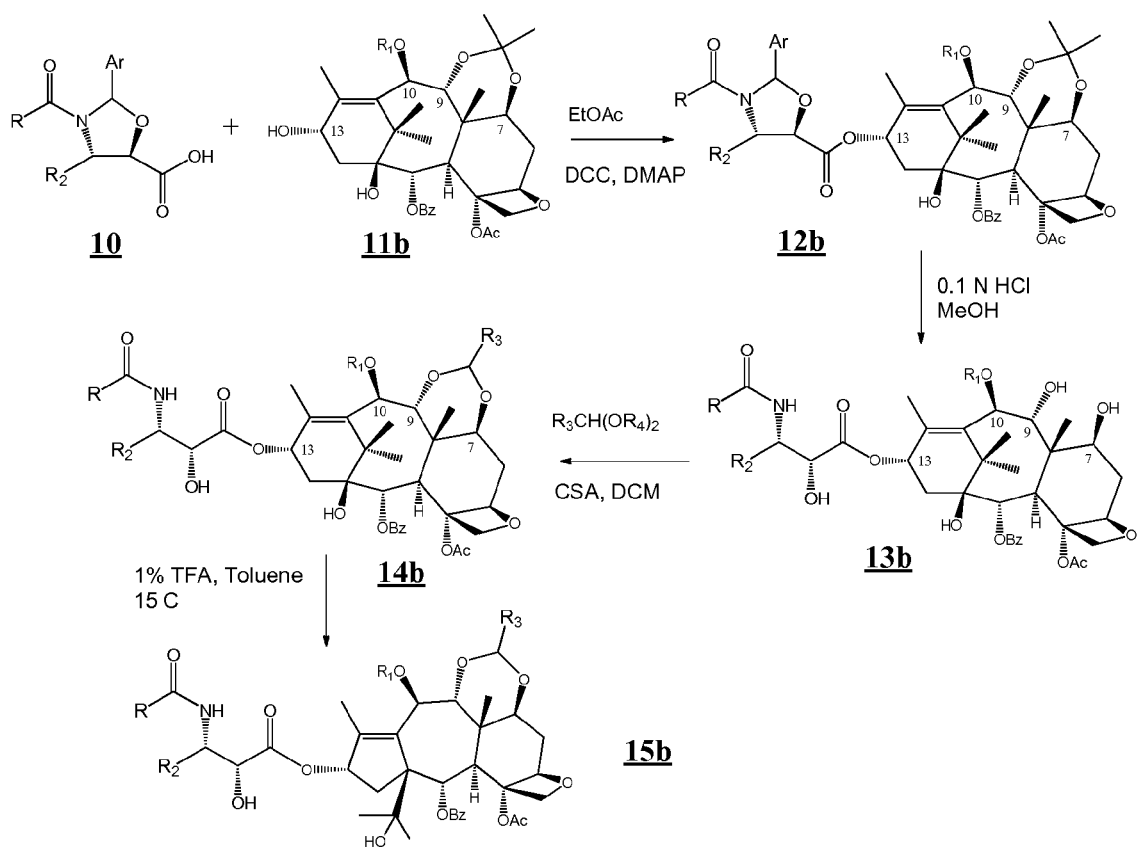
FIG. 2 depicts a representative process for preparing 10 beta taxane and abeo-taxane compounds of the present application.
Figure 3:
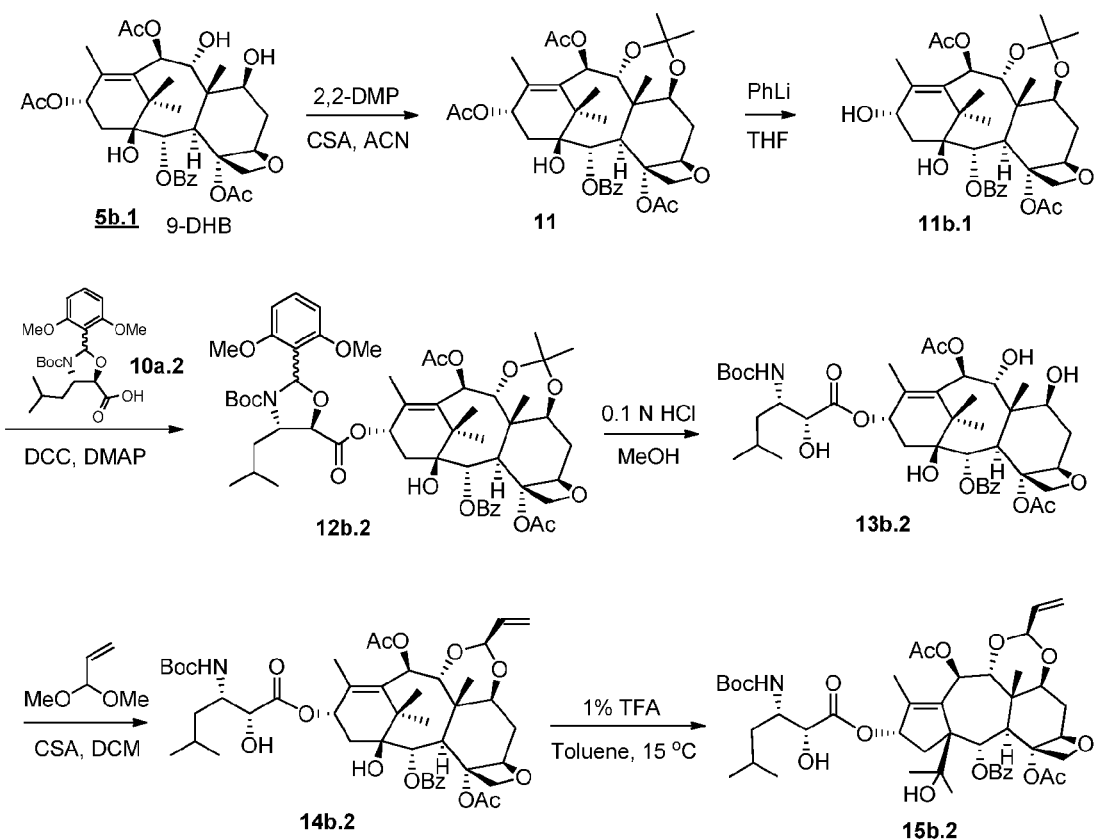
FIG. 3 depicts a representative process for preparing a 10-beta taxane and abeo-taxane derivative from a 9-DHB derivative.

In one variation, the 10-beta compounds of the present application can be prepared by the steps as outlined below. See also FIGS. 2 and 3.

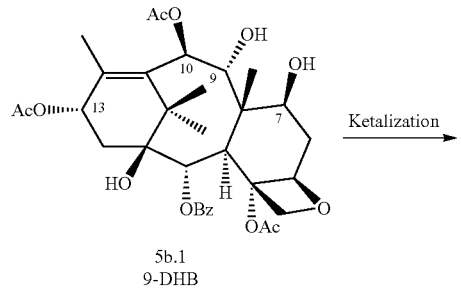

5b.1
9-DHB

Ketalization

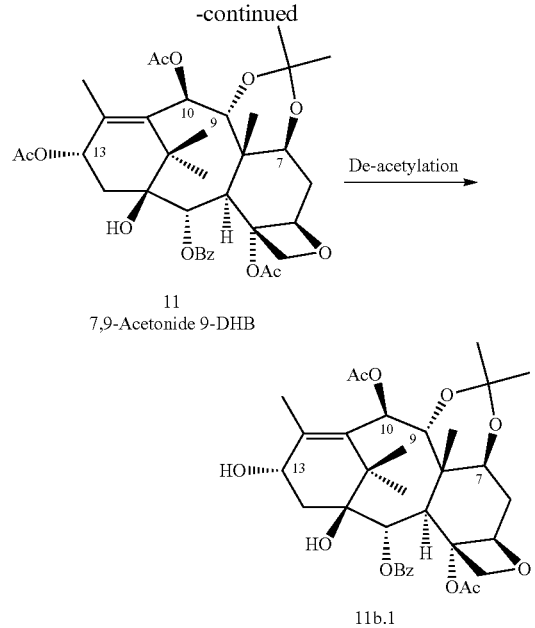

11
7,9-Acetonide 9-DHB

De-acetylation 11b.1

9-DHB 7,9-Ketal:

630 mg of 5b.1 9-DHB (13-acetyl-9-dihydrobaccatin III, 1 mmol) was weighed into a 25 ml RB flask, 7 ml of ACN was added at room temperature and the resulting mixture was stirred. 2.44 ml (~20 mmol) of 2,2-dimethoxypropane was added followed by 126 mg of montmorrilonite clay. Stirring was continued under nitrogen. The reaction progress was monitored by TLC (15:85 acetone:DCM) after about 135 minutes; which suggested that reaction was about 50% complete. The reaction had not progressed after another 2 hours of stirring. 15 mg of camphorsulfonic acid was added and stirring was continued. After 45 minutes, TLC indicated all starting material was consumed. The reaction was quenched by adding 450 mg of solid $K_2CO_3$ and the resulting mixture was stirred for 15 minutes. 3 ml of water was added and stirring continued for another 10 minutes. The slurry was filtered on a sintered funnel and the filtrate evaporated on the rotavapor. The water was azeotroped with acetonitrile and the resulting product dried in an oven overnight. The crude product was purified on a flash column with 1:9 acetone:DCM to give 550 mg of product 11.

13-Deacetylation:

450 mg (0.67 mmol) of 7,9-acetonide-9-DHB, 11 was added to a RB flask, and 15 ml of THF was added and the solution stirred under nitrogen and cooled to −50° C. 1.6 ml of (1.8 M) phenyl lithium was added dropwise over a period of 8 minutes. TLC of the reaction with 4:6 EtOAc, heptanes after 10 minutes indicated the reaction was complete. The reaction mixture was poured into a 50 ml solution of saturated aqueous ammonium chloride and allowed to rise to room temperature. The layers were partitioned and the mixture was extracted thrice with 20 ml of isopropyl acetate. The organic layers were combined, washed with brine, dried over $Na_2SO_4$ and concentrated. The crude product was dried in the oven overnight. Purification by silica gel chromatography using 40:60 EtOAc, Heptanes with 1% AcOH and 1% water gave purified product (11b.1) which was taken into the next step.

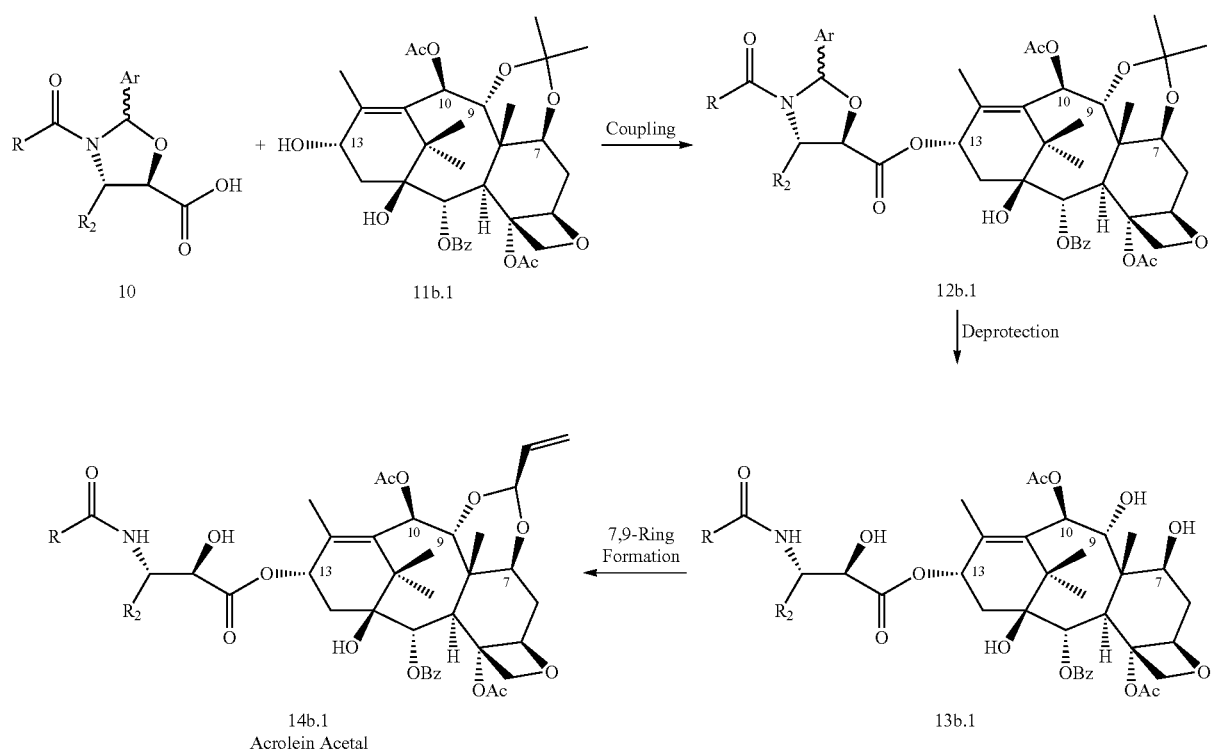

Coupling Reaction:

In a RB flask 469 mg (1 mmol) of protected side chain for coupling, 10, 630 mg (1 mmol) of protected 13-hydroxy-10-beta acetyl baccatin derivative (11b.1), 61 mg (0.5 mmol) of DMAP were weighed and the flask capped with a septum. 15 ml of dry EtOAc were added and the mixture stirred under $N_2$ at room temperature and 206 mg (1 mmol) of DCC were added. The reaction was stirred for 45 minutes and checked with TLC indicating it was about 60% complete. After another 1 hour, TLC indicated little change. Another 50 mg of DCC and 200 mg of the protected side chain, 10, was added and stirring continued for 2 more hours. TLC showed the reaction complete (complete conversion of 11b.1). The reaction was quenched by adding 5 ml of water and 20 ml of ammonium chloride and partitioned and the organic layer separated, washed with 25 ml of brine, dried over sodium sulfate and concentrated on the rotavapor. The crude product was purified by flash chromatography with 1:3 EtOAc/heptanes to give purified coupled ester, 12b.1.

Acetal Deprotection:

1.5 gm of the coupled ester (1.39 mmol) was weighed into a 100 ml RB flask with a reflux condenser, and 30 ml of MeOH were added and the mixture stirred under nitrogen. The flask warmed to 45° C. and 10 ml of 0.1 N HCl were added dropwise over a period of 10 minutes. Stirring was continued after the addition and the reaction monitored by TLC until the starting material was converted to slower spot on TLC. The reaction was cooled to room temperature and quenched with aqueous sodium bicarbonate until the pH was about 9. MeOH was evaporated on a rotary evaporator and 50 ml of EtOAc was added to the flask. The mixture was partitioned and the EtOAc removed. The aqueous layer was extracted twice more with 50 ml EtOAc. The organic layers were combined, washed with 50 ml brine and concentrated to give crude product which was purified by flash chromatography using 1:1 EtOAc:Heptanes. 900 mg of product 13b.1 was obtained.

Clay Catalyzed Acrolein Acetalization Reaction:

0.16 gm of 13b.1 (0.192 mmol) and 42 mg of acrolein dimethyl acetal (0.41 mmol) were weighed into a 25 ml RB flask followed by addition of 40 mg of Montmorillonite clay, the flask was capped with a septum and 3 ml of ACN were added under nitrogen. The pH of the reaction was determined to be about 6. About 3 microliters of TFA were added. After additional stirring, the pH was found to be 3.5. After 30 minutes, 0.15 ml of acrolein dimethyl acetal was added and stirring continued at room temperature. The reaction was monitored by TLC and HPLC. The reaction was quenched after stirring for 5 hours with 2 ml of aqueous sodium bicarbonate and the solution was filtered over a bed of celite. The celite bed was washed with 20 ml of ACN, and the filtrates combined and concentrated on the rotavapor. The crude product was purified by reverse phase chromatography using methanol/water 4:1 to give 150 mg of acrolein acetal product, 14b.1.

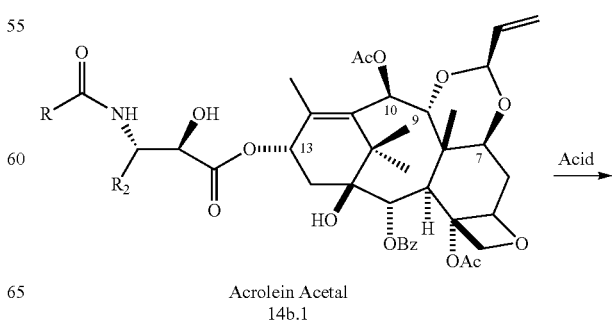

Acrolein Acetal
14b.1

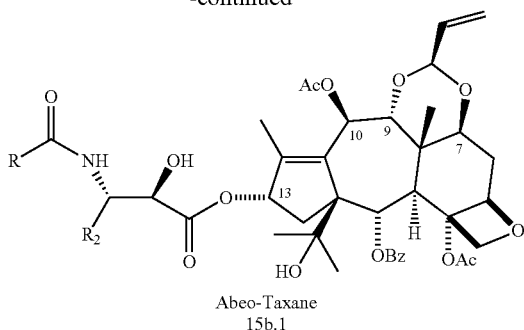

Abeo-Taxane
15b.1

Abeo-Taxane Formation:

To 0.125 gm of acrolein acetal starting material, 14b.1, contained in a RB flask was added 5 ml of wet toluene (toluene stored in a bottle containing 2 ml of water at the bottom so the solvent was saturated with water). The contents of the flask were stirred and cooled to 14° C. in a water bath containing some ice. 5 ml of 2% TFA in toluene were added over a minute to the flask and stirring continued. The reaction was monitored by HPLC by the taxane method which indicated the starting material conversion to product with retention time of 10.7 minutes. The reaction was quenched after 120 minutes with 5 ml of aqueous sodium bicarbonate. The toluene layer was separated and the bicarbonate layer separated with 20 ml of EtOAc. The organic layers were combined washed with 20 ml of brine, dried over sodium sulfate and concentrated on the rotavapor. The crude product was dried in the oven overnight and purified by reverse phase chromatography with 4:1 MeOH, water to give 58 mg of abeo-taxane rearranged product, 15b.1.

Example 2

Figure 4:
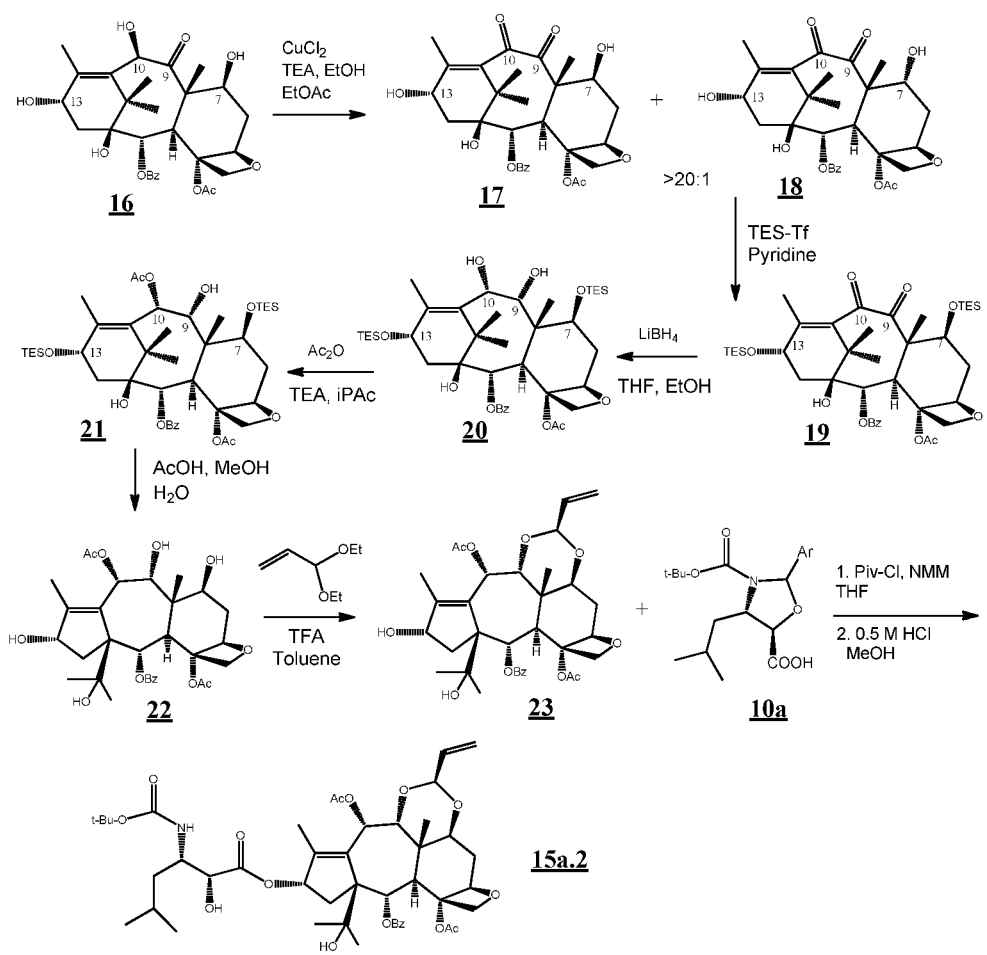
FIG. 4 depicts a representative process for preparing a 10-alpha abeo-taxane derivative from a baccatin derivative.

In one variation, the 10-alpha compounds of the present application can be prepared by the steps as outlined below. See also FIG. 4.

Oxidation of 10 DAB III 16:

A 4 L reaction flask, rinsed with 300 mL dried EtOAc and held under $N_2$, was charged with 1250 mL dried EtOAc. The resulting mixture was stirred, and dried 16 (100 g, 0.184 mol) was added. The addition of 800 mL USP EtOH followed and the reaction mixture was cooled to −1.3° C. Anhydrous $CuCl_2$ (86.4 g, 3.5 eq.) was added and solids were washed into the mixture with 450 mL anhydrous EtOH. The reaction mixture was cooled to ≤−13° C. and anhydrous TEA (90 mL, 3.5 eq.) was added slowly. The reaction was monitored by HPLC/TLC. At 1 h the reaction was judged complete (<5% starting material). 36 mL TFA was added to quench the reaction and stirring continued for 15 min. The reaction mixture was transferred to a 10 L rotovap flask. 500 mL EtOAc and 300 mL EtOH were added to the reaction flask, stirred for 2 min and the rinse added to the contents of the rotovap flask, which was evaporated on the rotavap at 40° C. until no further distillation occurred (80 min). Acidified ethanol (1% acetic acid, 300 mL) was added to the residue and the resulting slurry was transferred to a 2 L rotovap flask. The first rotovap flask was rinsed into the second with 400 mL acidified EtOH. The mixture was evaporated on the rotavap at 40° C. Acidified ethanol (305 mL) was added to the rotovap flask and the mixture was stirred at 40° C. for 10 min. The flask were then cooled to 5° C. and filtered. The rotovap flask was rinsed 2×300 mL cold (2° C.) acidified ethanol and the rinse was transferred to the filter to wash the solids. The solids were dried in the vacuum oven overnight at 45° C. to give 17. HPLC Area %=91.3%. Yield=96.7 g.

Silylation of 17 to Form 19:

To 17 (96.72 g, 0.1783 mmol) in a 10 L rotovap flask was added ethyl acetate (3000 mL, 30 mL/g). The solution was evaporated on the rotovap at 40° C. to approximately half the original volume (distilled volume=1680 mL). 1000 mL toluene (10 mL/g) was added to the remaining solution and rotovaped at 40° C. until solids were obtained (45 min). The solids were suspended in toluene (1000 mL, 10 mL/g) and the suspension was rotoevaporated at 40° C. (~1 h) to dry solids. The solids were transferred to a 2 L flask under $N_2$ stream. The solids were rinsed into the reaction flask with anhydrous pyridine (292 mL, 3 mL/g) and the resulting mixture was stirred. Upon dissolution, the contents were cooled to −20° C. Triethylsilyl trifluoromethanesulfonate (TES-OTf, 120.9 mL, 3.0 eq.) was slowly added to the reaction mixture to maintain at ≤−10° C. After the addition of TES-OTf, the mixture was allowed to warm to −5.8° C. 30 mins after the addition of TES-OTf, sampling was begun at thirty-minute intervals for HPLC/TLC. The reaction was judged complete at 2 h when HPLC/TLC indicated <2% mono-TES derivative remaining. The mixture was cooled to −17.5° C., methanol (19.3 mL, 0.2 mL/g) was added and stirred for 5 min. The mixture was warmed to room temperature, 500 mL MTBE was slowly added and then transferred to a separatory funnel. Residues in the reaction flask were washed into the separatory funnel with MTBE (200 mL, 2 mL/g), then water (250 mL, 2.5 mL/g) and saturated $NH_4Cl$ solution (250 mL, 2.5 mL/g) were added. The organic layer was transferred to a clean container. MTBE (250 mL, 2 mL/g) was added to the aqueous layer. It was agitated and the layers were separated. The second organic layer was washed with 100 mL MTBE and water (200 mL, 2 mL/g) was added to the combined layers. The organic layer was transferred to a 2 L rotovap flask and evaporated to a residue at 40° C. n-Heptane (500 mL, 5 mL/g) was added and the solution was evaporated to a residue at 40° C. n-Heptane (1000 mL, ~10 mL/g) was added and the solution was evaporated to one-half of its volume (distilled volume=375 mL). n-Heptane (300 mL, ~2.5 mL/g) was added and stirred on a rotavap at 40° C. The solution was cooled to −15.7° C. while stirring was continued for ~2.5 h and then filtered. The solids were rinsed into the filtration funnel with cold (<5° C.) n-heptane (100 mL) and collected and dried in the vacuum oven to give 111 g 19. HPLC Area % purity=93.4%.

Reduction of 19 to Prepare 20:

To a stirred solution of THF (560 mL, 5 mL/g) under $N_2$ in a 4 L reaction flask, was added 19 (111 g, 0.144 mol,) followed by anhydrous ethanol (560 mL, 5 mL/g). The mixture was stirred to dissolve the solids and then cooled to −12° C. 2 M $LiBH_4$ in 72 mL THF was added to control the reaction temperature (temp=−11.9 to −9.7° C.). The reaction was sampled for HPLC/TLC at 30 min intervals. Additional 2 M $LiBH_4$ in THF was added (72 mL, 1.0 eq.) to the reaction flask (temp=−9.6° C. to −7.1° C.) and stirred for 30 min. A third addition of 2 M $LiBH_4$ in THF (36 mL, 0.5 eq.) was made as before (temp=−7.6° C. to −6.7° C.), but with the bath temperature adjusted to 15° C. following the addition of the $LiBH_4$ solution and to 12.5° C. ten minutes later. At 1 hr after $LiBH_4$ addition, the reaction was complete (mono reduced product ≤3% relative to 20). The mixture was cooled to −10.8° C. and 10% ammonium acetate in 560 mL EtOH was added to allow the foam to settle and to control the temperature of the solution ≤−3° C. The mixture was transferred to a 2 L rotovap flask and residues were rinsed into the rotovap flask with 250 mL EtOH and content was evaporated on the rotovap at 40° C. to an oil, and 560 mL Methanol was added. 1700 mL water was added to a 5 L flask and was vigorously agitated. To precipitate the product, the methanol reaction mixture (748 mL) was added to the flask containing water. The mixture was filtered and the solids were washed with 650 mL water. The solids were vacuum dried overnight at 45° C. to give 140 g of slightly wet non-homogeneous product, 20. HPLC area % purity=92.8%.

Acetylation/Deprotection of 20 to prepare 22:

Acetylation: To 20 (138 g, 0.178 mol) in a 2 L rotovap flask was added IPA (isopropyl acetate, 1400 mL, 10 mL/g). The solution was rotoevaporated at 40° C. to an oil. The procedure was repeated. 550 mL dried IPA was then added to the oil and the contents were transferred to a 1 L reaction flask under $N_2$. The rotovap flask was washed into the reaction flask with 140 mL IPAc. DMAP (8.72 g, 0.4 eq.), anhydrous TEA (170 mL, 7 eq.) and acetic anhydride (100.6 mL, 6 eq.) were added and the mixture was stirred and heated to 35° C. The mixture was heated to 35° C., the reaction was monitored by HPLC/TLC. Upon completion of the reaction, as indicated by the absence of 20 (3 h total time), the mixture was cooled to 19.7° C. and saturated ammonium chloride solution (552 mL) was added. After stirring for 15 min, the mixture was transferred to a separatory funnel, the layers were separated. 280 mL water was added to the organic layer and the mixture was stirred for 4 min. and the layers were separated. The organic layer was transferred to a 2 L rotovap flask and the remaining content of the separatory funnel was washed into the rotovap flask with 200 mL IPA. The mixture was evaporated to dryness at 40° C. to give 124 g 21 as pale yellow oily foam.

Deprotection: To the rotovap flask containing 21 (124 g) was added methanol (970 mL, 7 mL/g). Sampling for HPLC/TLC was begun and continued at 1-hour intervals. The 21/methanol solution was transferred to a 3 L reaction flask and agitation was begun. The remaining content of the rotovap flask was washed with 400 mL methanol. Acetic acid (410 mL, 3 mL/g) and water (275 mL, 2 mL/g) were added and the reaction mixture was heated to 50° C. to 55° C., and the reaction was monitored by HPLC/TLC at 1-hour intervals for formation of the product, 22. Upon completion (~9 h), the mixture was cooled to rt and transferred to a 10 L rotovap flask. Solvent exchanges to n-heptane (2×1370 mL, 1×1000 mL) and IPA (2×1370 mL, 1×1500 mL) were performed. IPA (280 mL, 2 mL/g) and silica (140 g, 1 g/g) were added and the contents rotoevaporated at 40° C. until free flowing solids were obtained. The dry silica mixture was loaded onto a silica pad (7 cm column, 280 g silica), conditioned with 2:1 n-heptane/IPA (500 mL, 2 mL/g silica) and washed (4×) with 2:1 n-heptane/IPA, 2 mL/g silica, 3400 mL total) and (4×) with 1:1 n-heptane/IPA (3020 mL total, 2 mL/g silica) until all impurities were removed as indicated by TLC. Each wash (~840 mL) was collected as a separate fraction and analyzed by TLC. The silica pad was then washed (5×) with waEtOAc (1% water, 1% AcOH in EtOAc) (3950 mL total, 2 mL/g silica) and with 1:1 MeOH/EtOAc and each wash (~840 mL) was collected. The fractions containing 22 as indicated by HPLC/TLC were combined and rotoevaporated to dryness at 40° C. The residue in the flask was dissolved and evaporated to dryness: first with 1055 mL IPA and 550 mL n-heptane and a second time with 830 mL IPA and 410 mL n-heptane. 500 mL IPA was then added to the residue, the solution was transferred to a 2 L round bottom flask and 140 mL n-heptane was added. The resulting solution was rotoevaporated at 40° C. to give 22 as foam. 160 mL IPA was added to the flask followed by 800 mL toluene. The solution was rotoevaporated under vacuum at 50° C. until half of the solvent was removed. The flask were stirred and cooled to 21° C. for 1.5 h. The solids were filtered and were washed with 165 mL toluene and dried at 40° C. to give 62.6 g of 22. HPLC area %=96.9%

Acetal Formation: Compound 22 to 23

To a 3 L reaction flask containing 22 (25 g, 42.4 mmol) was added 375 mL toluene and the reaction was cooled to ~−15° C. TFA (9.8 mL, 3.0 eq.) was slowly added, followed by the addition of acrolein diethyl acetal (8.7 g) and the reaction was monitored by HPLC until <3% of 22 remained. Hydrated silica was prepared by mixing silica (25 g) and water (25%) and a "basified silica" mixture was prepared by mixing a solution of $K_2CO_3$ (17.6 g, 3.0 eq.) in water (1 mL/g 22) with 50 g silica. Upon reaction completion, the hydrated silica was added to the reaction mixture and it was stirred for 30-45 min at ≤5° C. The basified silica was then added to the mixture at ≤5° C. and the pH >5. After stirring for ~15 min, the mixture was filtered. The silica was washed with ~20 mL/g toluene and the filtrates were combined and concentrated. The residue was digested with 1 mL/g toluene for ~4 h. The resultant solids were filtered and washed with 80:20 toluene/heptane to give 25 g of 23. HPLC area %=98%. Mass yield=66%.

Preparation of Compound 15a.2 from 23:

To THF (300 mL, 8 mL/g) stirring in a 1 L reaction flask (rinsed with 500 mL THF) was added 23 (35.7 g, 0.0570 mol). Purified coupling agent 10a (30.9 g, 1.25 eq.) was added to the reaction mixture followed by the addition of NMM (11.5 mL, 1.8 eq.), DMAP (2.77 g, 0.4 eq.) and THF (75 mL, 2 mL/g). The mixture was stirred while $N_2$ was bubbled from the bottom of the flask to mix and dissolve the solids. Pivaloyl chloride (11.5 mL, 1.6 eq.) was then added to the reaction mixture. The mixture was warmed to 38° C.±4° C. After 1 h the reaction was cooled to 2° C. 0.5 N HCl in MeOH (280 mL, ~20 mL/mL NMM) was added to maintain the pH=1.5-1.9. The mixture was stirred at 2° C.±2° C. and monitored by HPLC/TLC at 30 min intervals for formation of 15a.2 and the acrolein acetal hydrolyzed by-product. After 2 hr 300 mL 5% aqueous sodium bicarbonate and IPAc (185 mL, 5 mL/g) was added. The reaction mixture was transferred to a 2 L rotovap flask and rinsed with 2× with 60 mL IPAc. The mixture was evaporated at 40° C. to an oil and water was obtained. 200 mL IPAc was added and the contents were transferred to a separatory funnel. The reaction flask was rinsed with 100 mL IPAc and the layers were separated. 70 mL water was added to the organic layer and the layers were separated. The organic layer was rotoevaporated at 40° C. to a foam, and dried in the vacuum oven to give 64.8 g crude 15a.2. HPLC area %=45.5%.

Purification Procedures:

Normal Phase Chromatography: The 6" Varian DAC column was packed with Kromasil (5 Kg, 10 μm, 100 Å normal phase silica gel). The 50-cm bed length provided a 9 L empty column volume (eCV). The column had been regenerated (1 eCV 80:20 waMTBE:MeOH) and re-equilibrated (1 eCV waMTBE, 1 eCV 65:35 n-heptane:waMTBE). The crude 15a.2 (64.7 g), was dissolved in MTBE (180 mL) and heated to ~40° C. 280 mL n-Heptane was added to the solution, and was pumped onto the column. The column was then eluted with 65:35 n-heptane:waMTBE at 800 mL/min. A 34 L forerun (~3.8 eCV) was collected followed by 24 fractions (500 mL each). Fractions 1 through 23 were combined and concentrated to dryness on a rotovapor. The residue was dried in the vacuum oven overnight to provide 41.7 g 15a.2. HPLC area %=99.4%.

Final Purification: The normal phase pool was dissolved in USP EtOH (6 mL/g) and concentrated to dryness three times. The residue was dissolved in USP EtOH (2 mL/g). This ethanolic solution was slowly added drop-wise to water (deionized, 20 mL/g) with stirring. The solids were vacuum filtered and washed with cold DI water, and dried in the vacuum oven at 40° C. overnight to give 38.9 g 15a.2. HPLC area %=99.5%.

Separation of Diastereoisomers of Formula 15a.2 by Normal Phase Chromatography

The compound of formula 15a.2, (570 mg) which comprises a mixture of diastereoisomers is dissolved in 35:65 MTBE/n-heptane. The solution is loaded onto a flash chromatography column packed with spherical silica (YMC-1701, 56 g), which has been conditioned with 35:65 MTBE/n-heptane. The column is eluted with 35:65 MTBE/n-heptane and fractions (25 mL) collected. Fractions containing the pure product are collected, pooled and concentrated to the diastereoisomer of 15a.2 as a white solid.

Example 3

In one variation, the 10-alpha compounds of the present application can be prepared by the steps as outlined below. See also FIG. 5.

Figure 5:
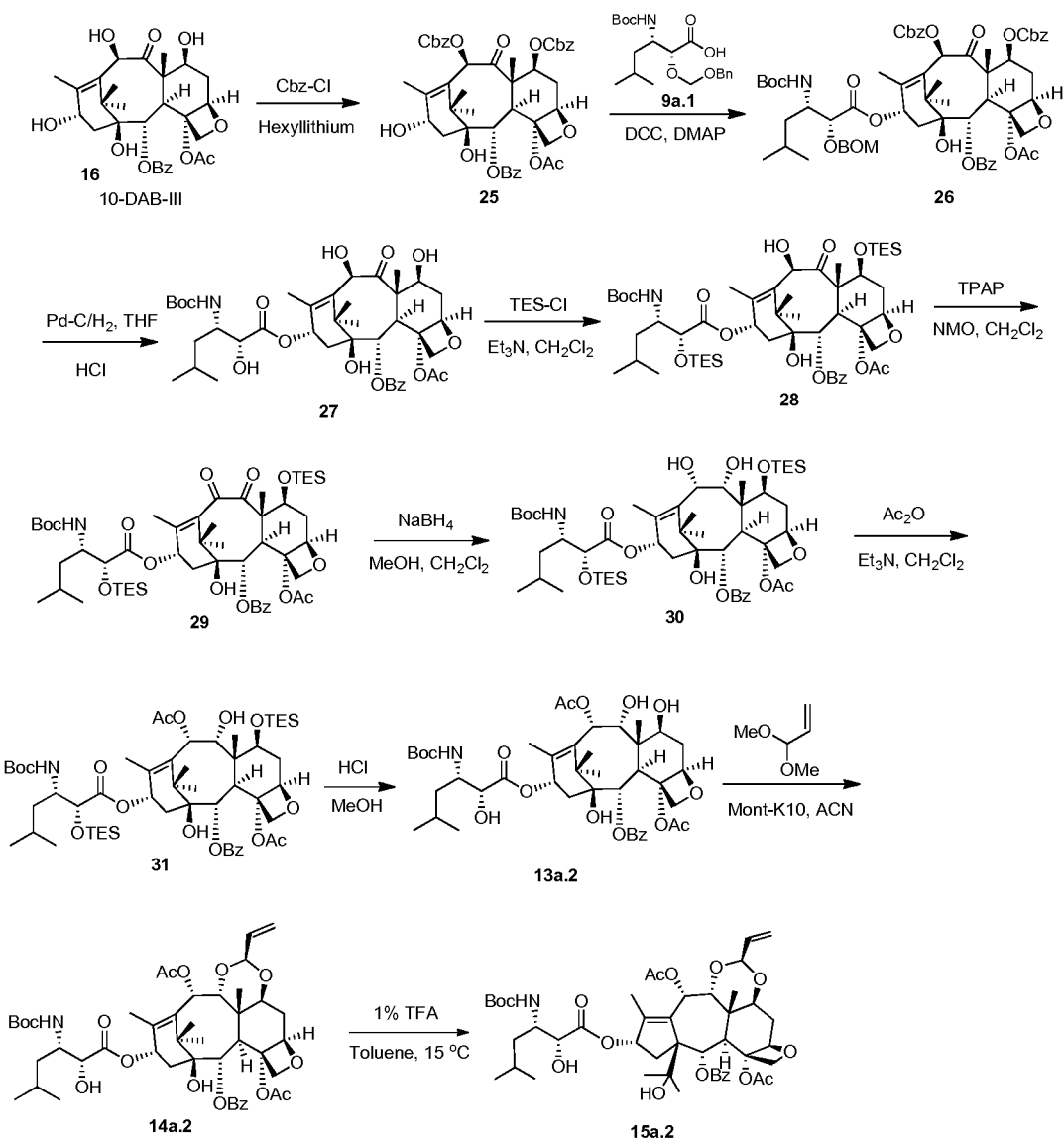
FIG. 5 depicts a representative process for preparing a 10-alpha taxane and abeo-taxane derivative from a baccatin derivative.
Figure 6:
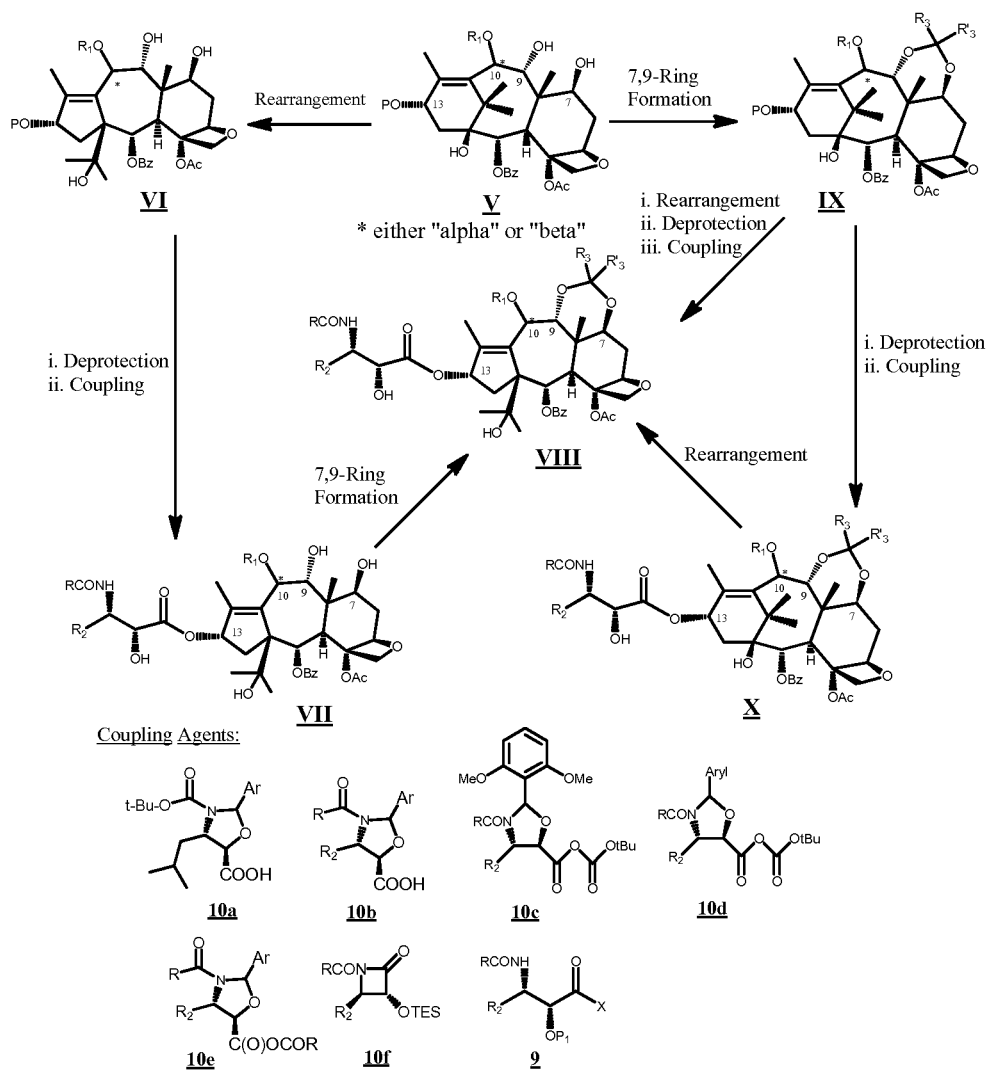
FIG. 6 depicts a general synthetic scheme illustrating representative processes for the preparation of the compounds of the present application.

7,10-di-CBZ Protection of 10-DAB III:

10-Deacetylbaccatin III (10-DAB III), which has formula 16 as shown in FIG. 5, (Sigma-Aldrich) was used as an intermediate in the preparation of various taxanes. 10-DAB III, formula 16, is first protected at both the C-7 and C-10 positions to form the C7, C10 di-CBZ derivative of formula 25. 10-Deacetyl baccatin III of formula 16 (50 g, 91 mmol) was dissolved in THF (2 L, 40 ml/g) by warming to 40° C. The solution was cooled to −41° C. and benzylchloroformate (46 mL, 3.2 eq, 294 mmol) was added followed by further cooling to −44° C. 2.3M hexyl lithium solution (130 mL, 3.3 eq, 303 mmol) was added over 45 min at ≤−39° C., and stirred for 45 minutes. After two hours, 1N HCl (400 mL) and IPAc (1 L) was added and warmed to 10° C. The layers were separated and the IPAc layer was washed with $H_2O$ (500 mL), saturated $NaHCO_3$ (200 mL) and $H_2O$ (4×500 mL) and then filtered through a silica gel pad. The filtrate was concentrated until solids started to form. IPAc (850 mL) was added and the mixture was heated to 60° C. Heptanes (800 mL) were added and the solution was cooled and filtered. The solids collected by the filtration were washed with heptanes and dried under vacuum at 45° C. to give formula 25:

Coupling of Compound 25 and 9a.1:

Next, the compound of formula 25 was coupled with a side chain to form the compound of formula 26. Here, the side chain of the compound of formula 9a.1, (38 g, 99.6 mmol) was dissolved in toluene to 0.095 g/mL. This solution was added to the compound of formula 25 (54.0 g, 66.4 mmol). The solution was heated in a warm-water bath and DMAP (8.13 g, 66.4 mmol) and DCC (25.3 g, 120 mmol) in toluene (540 mL) were added. After 3 hours, additional DCC (13.0 g) in toluene (140 mL) was added. After about 25.25 hrs, MTBE (450 mL) was added and the mixture was filtered through a pad of silica gel, washed with MTBE, ethyl acetate, and concentrated to give the compound of formula 26 as 61.8 g of an oil.

Deprotection of 7,10-Benzoyl Groups:

The compound of formula 26 was then deprotected at both the C7 and C10 to give the compound of formula 27. A solution of THF (300 mL) and conc. HCl (22 mL) was added to a solution of the compound of formula 26 (61.8 g, 52.5 mmol) in THF (15 mL/g, 920 mL) under nitrogen. A catalyst (10% Pd/C with 50% water, 99.1 g) was added and the flask was flushed with nitrogen three times and then with hydrogen three times. The reaction mixture was stirred under a hydrogen balloon for 21 hours. HPLC indicated that 38% by area of starting material still remained. Water (10 mL) was added and stirring continued. Twenty hours later, HPLC indicated the same amount of starting material still remaining. The reaction mixture was filtered through celite and washed with THF. Excess THF was removed; fresh catalyst (101 g) was added and the reaction mixture was re-charged. After another 24 hours, more catalyst (20 g) was added. After another hour, the reaction mixture was filtered through celite and washed through with IPAc. The combined filtrate was washed with $NH_4Cl$ solution (500 mL), water (500 mL), 5% $NaHCO_3$ (500 mL), $H_2O$ (300 mL), and brine (300 mL). The organic layer was dried, filtered, and concentrated to give a foam of the compound of formula 27 (42.5 g).

Disilylation of Compound 27:

The compound of formula 27 was then converted to the compound of formula 28. Formula 27 (41.4 g, 52.5 mmol) was dissolved in DCM (500 mL) at room temperature. In the case that the impurity was water, $Na_2SO_4$ was added to the solution, and the solution was filtered through filter paper into to a 2 L flask. The solids were collected and washed with DCM (250 mL) and the washings transferred into the flask. TEA (35 mL) followed by DMAP (1.28 g) and TES-Cl (~30 mL, 3.5 eq) were added to the solution and stirred. Additional TES-Cl (15 mL) and TEA (20 mL) were added, and after 6 hours HPLC indicated the reaction had gone to completion. The reaction was then quenched with ethanol (25 mL). The layers were separated and the organic layer was washed with saturated $NH_4Cl$ (~500 mL), and dried over $Na_2SO_4$ and concentrated. A flash column was packed with silica gel and wet with 8:2 heptane/IPAc (1.5 L). The solids were dissolved in 8:2 heptane/IPAc (250 mL) and filtered to remove solids. This solution was concentrated to ~100 mL and applied to the column. The column was eluted with 8:2 heptane/IPAc. Fractions with product were pooled and concentrated to give foam of formula 28 (24.5 g).

Oxidation of Compound 28:

The compound of formula 28 was then oxidized to form the compound of formula 29. Solid $Na_2SO_4$ was added to a solution of formula 28 (24.5 g, 24.0 mmol) and 4-methyl morpholine N-oxide (10.1 g, 84 mmol) in DCM (340 mL). The mixture was stirred for 1 hour and then filtered through 24 cm fluted filter paper into a flask. The $Na_2SO_4$ solids were washed with DCM (100 mL) and the washings transferred into the flask. Molecular sieves (6.1 g, 0.15 g/g) were added to the solution and stirring was begun. TPAP (1.38 g) was added and the reaction was allowed to stir under a $N_2$ blanket and monitored by HPLC. Additional TPAP (0.62 g) was added after 2 hours and again (0.8 g) after 15 hours. The reaction mixture was applied to a pad of silica gel (86 g), wet with 8:2 heptane/IPAc and eluted with IPAc. The fractions were collected and concentrated to an oil. 4-Methyl morpholine N-oxide (5.0 g) and DCM (100 mL) were added and stirred. $Na_2SO_4$ (13 g) was added to the mixture and filtered through filter paper. The $Na_2SO_4$ solids were washed with DCM (45 mL). Molecular sieves (5 g) and TPAP (1.03 g) were added to the solution and after 45 minutes, more TPAP (1.05 g) was added. A pad of silica gel was prepared and wet with 80:20 Heptane/IPAc. The reaction mixture was applied to the pad and eluted with IPAc. Fractions with product were collected and pooled and concentrated to give an oil product of formula 29 (21.8 g).

Reduction on Diketone 29:

The compound of formula 29 was reduced to form the compound of formula 30. $NaBH_4$ (365 mg, 6 eq) was added to a stirred solution of formula 29 (1.6 g) in ethanol (19 mL) and methanol (6.5 mL) cooled in an ice-water bath. After 1 hour, the mixture was removed from the ice-water bath and at 2 hours, the reaction was complete. The mixture was cooled in an ice-water bath and a solution of NH₄OAc in methanol (15 mL) was added followed by the addition of IPAc (50 mL) and H₂O (20 mL), and separated. The organic layer was washed with water (20 mL) and brine (10 mL), with water (15 mL) and brine (10 mL), and then twice with water (2×15 mL). It was dried over Na₂SO₄ and placed in the freezer overnight. A sample was taken for HPLC and the reaction was dried and the organic layer was concentrated on the rotary evaporator, placed in the vacuum oven to give a foam product of formula 30 (1.45 g).

Regioselective Acetylation of Compound 30:

The compound of formula 30 was then acylated to form the compound of formula 31. TEA (5.8 mL, 41.5 mmol), Ac₂O (2.62 mL, 27.7 mmol) and DMAP (724 mg, 5.5 mmol) were added to a solution of formula (11) (14.1 g. 13.8 mmol)) in DCM (50 mL). The reaction was stirred and sampled for HPLC. After 18.5 hours, additional TEA (1.5 mL) and Ac₂O (1 mL) were added. At 19 hours, the reaction mixture was diluted with IPAc (300 mL) and poured into 5% NaHCO₃ (100 ml). It was then stirred, separated, and the organic layer was washed with water (100 mL), saturated NH₄Cl (2×100 mL), water (3×50 mL) and brine (50 mL) and then filtered through Na₂SO₄. The mixture was concentrated to give a foam product of formula 31 (14.6 g).

Desilylation of Compound 31:

Next, the compound of formula 31 was converted to the compound of formula 13a.2. A quantity of formula 31 (3.0 g, 2.83 mmol) was weighed into a 100 mL flask. DCM (24 mL) followed by methanol (6 mL) were added to the flask, and camphorsulfonic acid (CSA) (0.0394 g, 0.17 mmol) was added. After 4 hours, 5% NaHCO₃ (15 mL) was added, and the mixture was shaken and transferred to a separatory funnel. The reaction flask was rinsed with 5% NaHCO₃ (25 mL) and the layers were separated. The organic layer was washed with brine, dried over Na₂SO₄, and concentrated. MTBE (3×25 mL) was added and the reaction mixture was concentrated to dryness to give 3.71 g foam. The foam was dissolved in MTBE (10 mL) and stirred. Heptane (50 mL) was added to the reaction solution. The solids were vacuum filtered and rinsed with heptane (720 mL). The solids were collected and dried in a vacuum oven at 40° C. to give the compound of formula 13a.2 (2.18 g).

Synthesis of 14a.2 and 15a.2:

The compound of formula 13a.2 was converted to the compound of formula 14a.2 and then to the compound of formula 15a.2 using the experimental conditions as described for the conversion of 13b.1 to 14b.1 and then to 15b.1

Example 4

Figure 7:
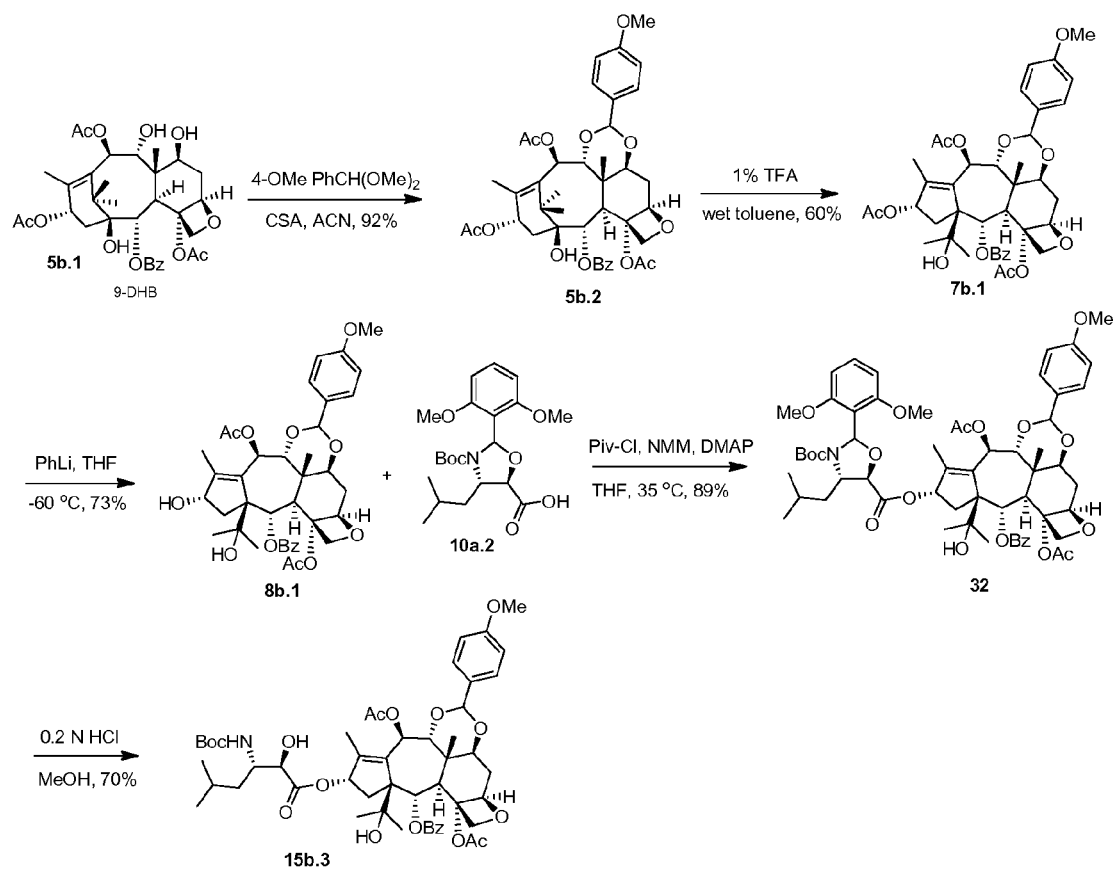
FIG. 7 depicts a representative process for preparing a 10-beta abeo-taxane compound.

In another variation, the 10-beta compounds of the present application can be prepared more efficiently by the steps as outlined below. See also FIG. 7.

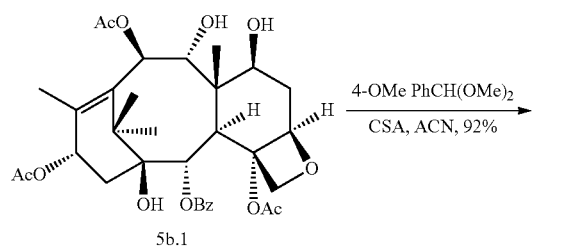

5b.1

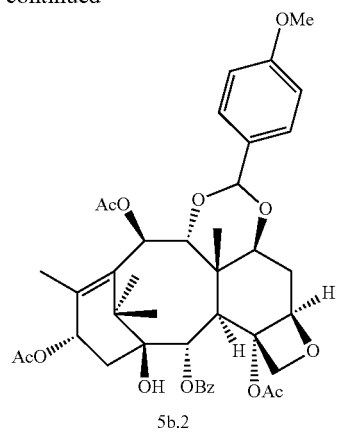

5b.2

9-DHB-7,9-PMB Acetal:

10.1 g of 5b.1 (9-DHB, 16 mmol) was weighed into a 250 ml RB flask, 40 ml of ACN was added at room temperature and the resulting mixture was stirred (9-DHB was not completely soluble at this concentration). 8.17 ml (48 mmol) of 4-methoxybenzyledene acetal was added followed by 149 mg of camphorsulfonic acid and stirred for 15 min. After 20 minutes, the mixture was poured into a 100 ml saturated sodium bicarbonate solution, and extracted with EtOAc (2×100 ml). The organic layers were combined, washed with brine, dried over Na₂SO₄ and concentrated. The crude product was purified on a flash column with 7:3 to 4:6 heptanes:EtOAc to give 11.9 of product 5b.2 in 92% yield.

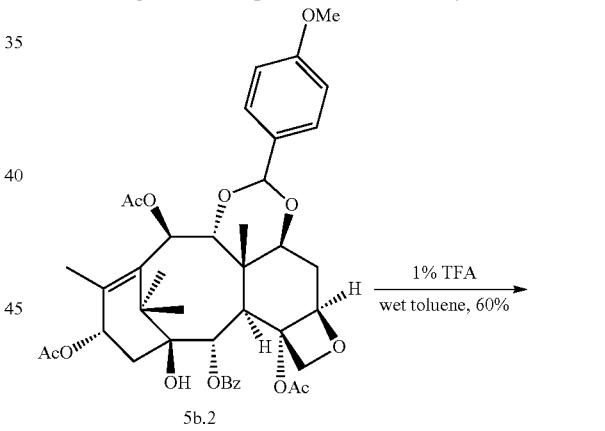

5b.2

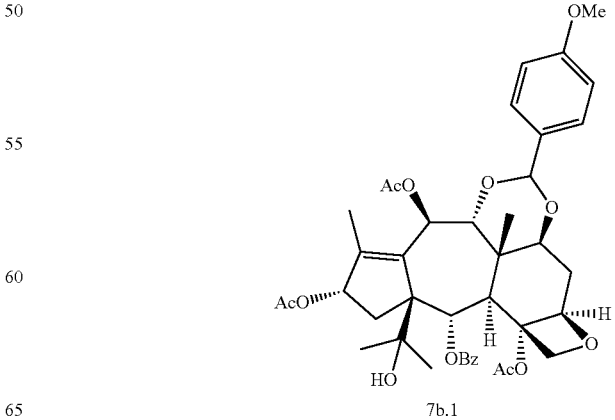

7b.1

Abeo-Taxane Formation:

To 12.2 g of compound 5b.2 (PMB acetal of 9-DHB, 16.3 mmol), contained in a RB flask was added 163 ml (0.1 molar concentration) of wet toluene (toluene stored in a bottle containing 5 ml of water at the bottom so the solvent was saturated with water). The contents of the flask were stirred and cooled to 14° C. in a water bath containing some ice. 163 ml of 2% TFA in toluene were added over a minute to the flask and stirring continued. The reaction progress was monitored by HPLC by the taxane_MKG10 method (Synergy column, ACN 60% 10 min, 2 min 100% CAN, 230 nm, 1.5 ml/min, 30° C.) which indicated the starting material retention time at 5.58 minutes and the product retention time at 5.80 minutes. The reaction was quenched after 4 hr 45 minutes (at this point HPLC analysis showed 5% starting material, 60% product and three side products at 3.70 (7%), 3.89 (26%) and 9.5 (2%) retention time) by pouring in 200 ml of saturated aqueous sodium bicarbonate solution. The toluene layer was separated and the bicarbonate layer was re-extracted twice with 100 ml EtOAc. The organic layers were combined, washed with 100 ml of brine, dried over sodium sulfate and concentrated on the rotavapor. The crude product was dried in the oven overnight and purified by normal phase chromatography using Kromasil normal phase silica gel (10 μm, 100 Å) in 6:4 heptane: EtOAc (EtOAc was saturated with 2% H$_2$O and 1% AcOH) to give 9.2 g (60%) abeo-taxane rearranged product 7b.1.

ice mixture). 37 ml of (66 mmol, 1.8 M solution in di-n-butylether) phenyl lithium was added dropwise over a period of 10 minutes. TLC of the reaction with 6:4 EtOAc:heptanes after 10 minutes indicated the reaction was complete. The reaction mixture was poured into a 150 ml solution of saturated aqueous ammonium chloride. The layers were partitioned and the mixture was extracted thrice with 100 ml of ethyl acetate. The organic layers were combined, washed with brine, dried over Na$_2$SO$_4$ and concentrated. The crude product was purified by flash chromatography using silica gel in 1:4 and 1:1 EtOAc, heptanes to give 5.4 g of 13-deacetyl product 8b.1 in 70% yield.

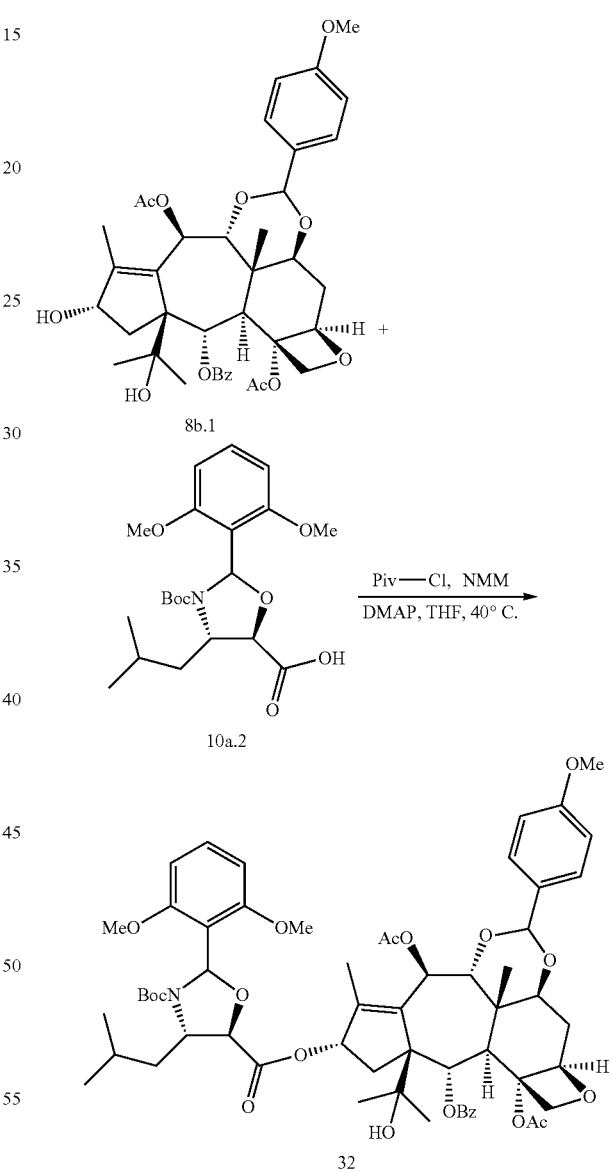

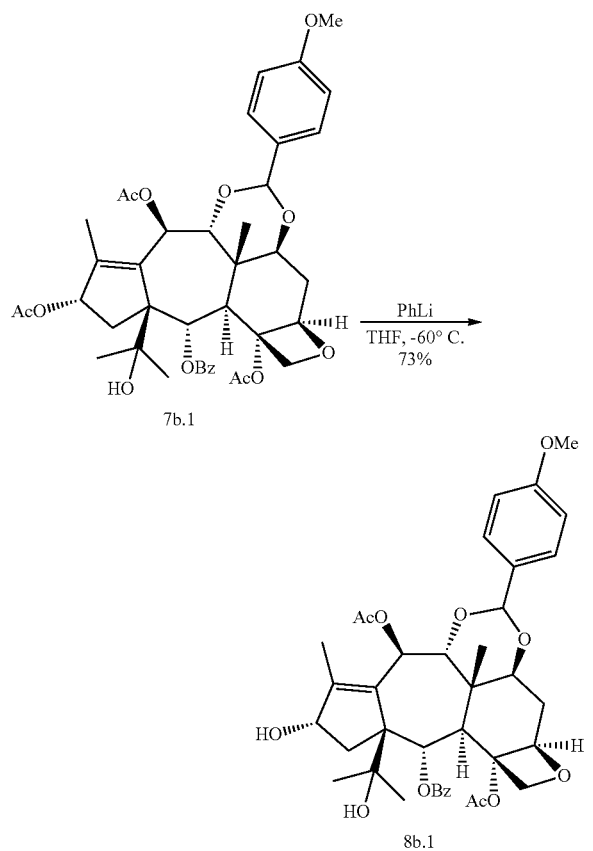

13-Deacetylation:

8.23 g (11 mmol) of 9-DHB-7,9-PMB acetal 7b.1 was dissolved in 220 ml (0.05 M) of anhydrous THF (HPLC grade THF over 4 Å° molecular sieves) was added and the solution stirred under nitrogen and cooled to −60° C. (by acetone-dry Coupling Reaction:

2.6 g of 2,6-dimethoxybenzylidene acetal protected side chain sodium salt 10a.2a was dissolved in EtOAc (25 ml) and poured into a of saturated sodium bisulfate solution (50 ml). The biphasic layers were mixed well in a separatory funnel for 5 minutes and the organic layer was separated, and washed twice with brine (20 ml). Organic layer was dried over sodium sulfate, evaporated under reduced pressure to obtain 2.5 g of the free acid 10a.2. 2.5 g (6.1 mmol) of acid 10a.2 2.4 g (3.4 mmol) of PMB protected 13-hydroxy-abeo-taxane 8b.1, 200 mg (1.7 mmol) of DMAP were weighed and the flask capped with a septum. 23 ml of dry THF and 1 ml (9.5 mmol) of N-methylmorpholine (NMM) was added and the mixture stirred under $N_2$ atmosphere. Reaction mixture was warmed to 35±4° C. and 1 ml (8.1 mmol) of trimethylacetyl chloride was added in 3 portions. The reaction was stirred for 30 minutes. THF was evaporated and the reaction mixture was poured in saturated sodium bicarbonate solution (25 ml) and extracted with EtOAc (2×20 ml). The combined organic layers were washed with brine (25 ml), dried over sodium sulfate and concentrated. The crude product was dried under high vacuum and purified by silica gel chromatography using 4:1 to 7:3 heptane:EtOAc to give 3.3 g of purified coupled ester 32 in 89% yield.

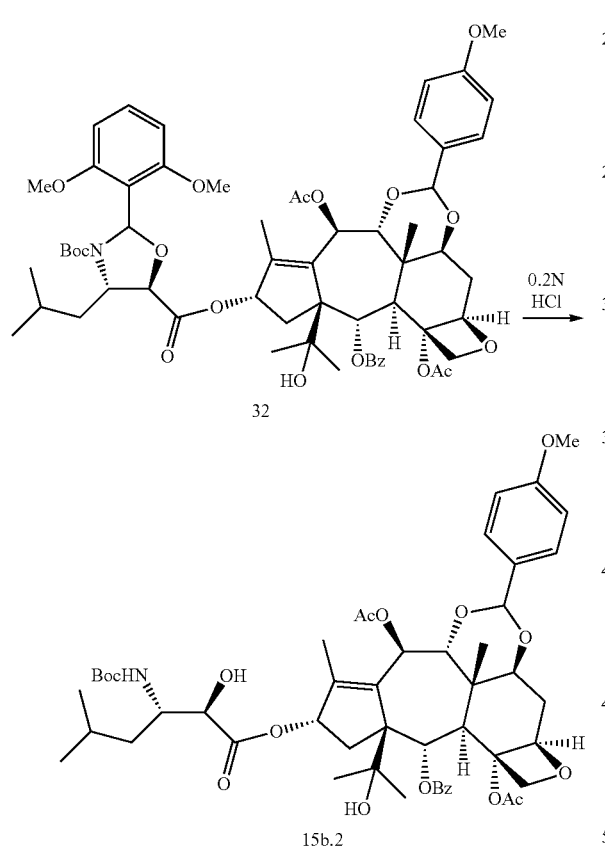

Ketal Deprotection:

0.22 g of the coupled ester 32 (0.2 mmol) was weighed into a 100 ml RB flask with a reflux condenser, and 6.6 ml (0.03 M) of MeOH was added and the mixture stirred under nitrogen. The flask warmed to 35° C.±4° C. and 2.2 ml of 0.1 N HCl was added dropwise over a period of 5 minutes. Stirring was continued until the starting material was completely consumed. The reaction was cooled to room temperature and quenched with aqueous sodium bicarbonate until the pH was about 9. MeOH was evaporated on a rotary evaporator and 15 ml of EtOAc was added to the flask. The reaction mixture was partitioned and the EtOAc layer was separated. The aqueous layer was extracted twice more with 15 ml EtOAc. The organic layers were combined, washed with 15 ml brine and concentrated to give crude product which was purified by flash chromatography using 7:3 hexanes:EtOAc to give 0.11 g of 15b.2 in 70% yield.

Example 5

Figure 1:
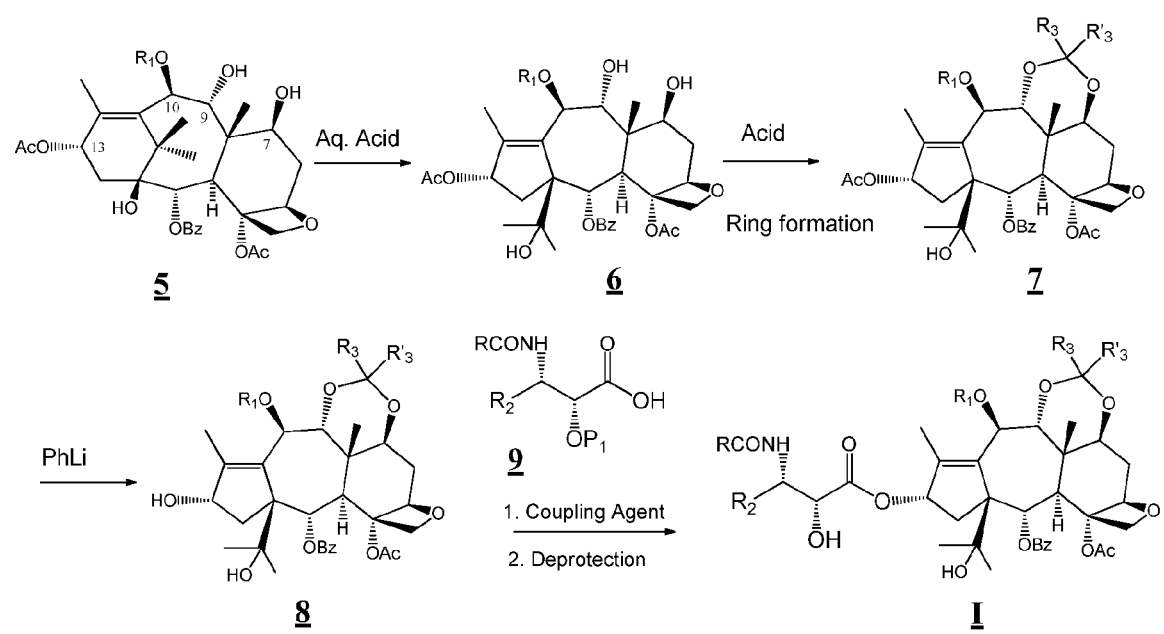
FIG. 1 depicts a representative process for preparing 10 beta abeo-taxane compounds of the present application.

In one variation, the process comprising the synthesis of various abeo-taxanes can be prepared efficiently from the corresponding taxanes as outlined below. See also FIG. 1.

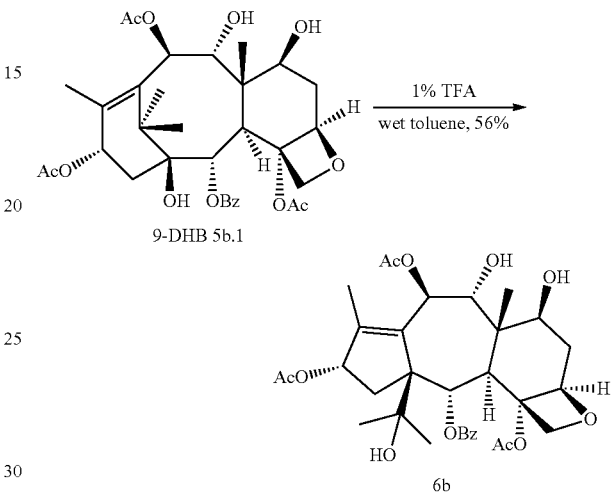

Direct Conversion of 9-DHB to Abeo-Taxane:

0.946 g of 9-DHB (1.5 mmol) was dissolved in 65 ml (0.0225 M) of wet toluene and the reaction flask was cooled to 15° C. in a water bath containing some ice. 65 ml of 2% TFA in wet toluene was added in one portion and the reaction was continued to stir at 15° C. The reaction progress was monitored in 15 minute time intervals by HPLC using taxane_MKG5 method (Synergy column, ACN:$H_2O$ 40:60 9 min, 2 min 100% ACN, 230 nm, 1.5 ml/min, 30° C.), which indicated the starting material retention time at 5.02 minutes and the desired product retention time at 5.98 minutes. The reaction was quenched after 1 hr 50 minutes (at this point HPLC analysis showed 10% starting material, 57% product and four side products with retention times 4.79 (9%), 4.09 (13%), 3.71 (7%) and 7.16 (4%) respectively) by pouring in 20 ml of saturated aqueous sodium bicarbonate solution. The toluene layer was separated and the bicarbonate layer was re-extracted twice with 10 ml EtOAc. The organic layers were combined, washed with 10 ml of brine, dried over sodium sulfate and concentrated on the rotavapor. The crude product was dried in the oven overnight and purified by normal phase chromatography using Kromasil normal phase silica gel (10 μm, 100 Å) in 45:55 heptane:EtOAc (EtOAc was saturated with 2% $H_2O$ and 1% AcOH) to give 0.52 g (56%) of rearranged product 6b.

Example 6

In one variation, 7,9-acetal/ketal analogs of the 10-beta taxanes can be prepared from the corresponding diol 13b.2 following the general procedure as outlined below.

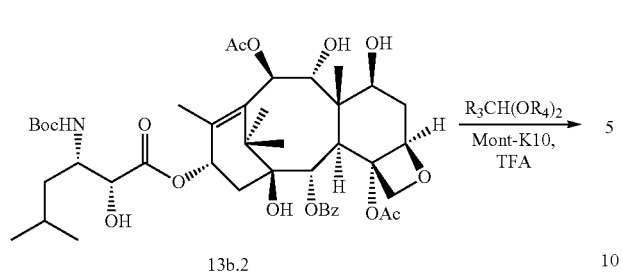

13b.2

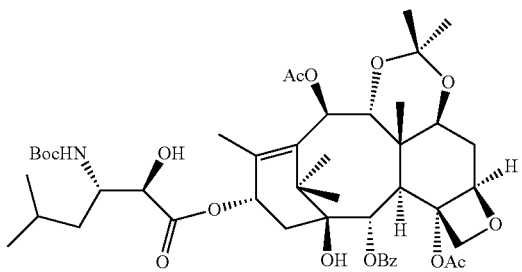

10-beta taxane-2,2-dimethylketal (14b.3)

+TOF MS: m/z 872.4307 [M+H]

14b

Acid Catalyzed Acetal/Ketal Formation of 10-Beta Taxanes:

25 mg of 13b.2 (0.03 mmol), 5 mg montmorillonite-K10 and 0.4 mmol of the corresponding dimethyl/diethyl acetal were weighed in an oven dried reaction flask equipped with a septa or a 4 ml vial with a Teflon cap. 1 ml of acetonitrile was added and the reaction mixture was stirred under nitrogen atmosphere at room temperature. The pH of the reaction was about 6. 1 to 2 microliters of TFA was added to bring the reaction pH to about 3-3.5. The reaction mixture was stirred about 2 to 5 hours and then quenched with 2 ml of aqueous sodium bicarbonate and the solution was filtered over a bed of celite, washed with 3×5 ml of ACN, and the filtrates were concentrated on the rotavapor. The crude product was purified by flash column chromatography on silica gel, using heptanes/EtOAc. The following acetals/ketals 14b have been prepared employing the above procedure in good yields (60-90%). All the compounds were characterized by the 1H NMR and HRMS and their purity was determined by HPLC.

10-beta taxane-2-methylpropenyl acetal (14b.4)

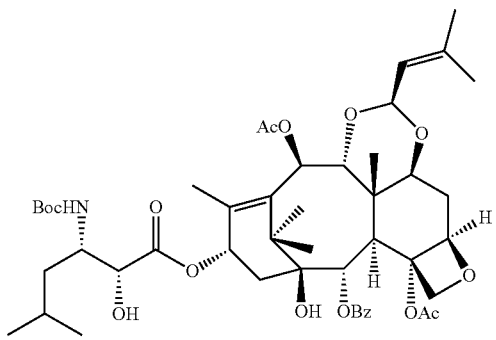

+TOF MS: m/z 898.4468 [M+H]

10-beta taxane 2,6-dimethyl-1,5-hepadienyl acetal (14b.5)

10-beta taxane acrolein acetal (14b.2)

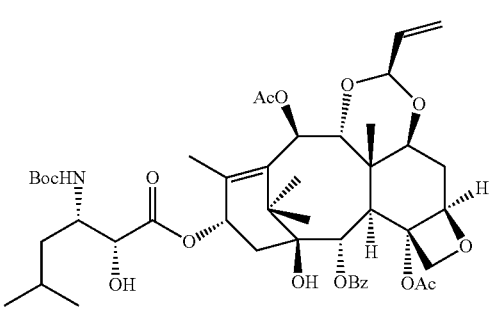

+TOF MS: m/z 870.4162 [M+H]

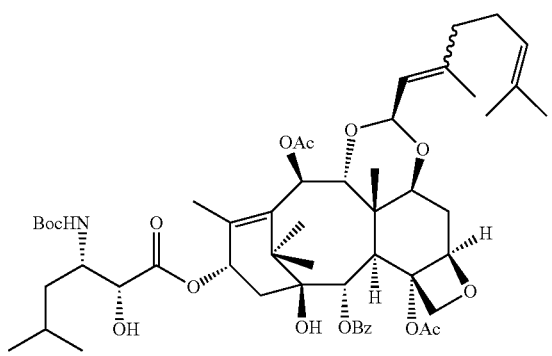

+TOF MS: m/z 966.5098 [M+H]

10-alpha taxane hexanal acetal (14b.6)

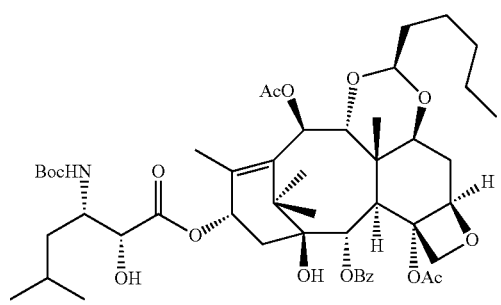

+TOF MS: m/z 914.4696 [M+H]

10-beta taxane benzylidene acetal (14b.7)

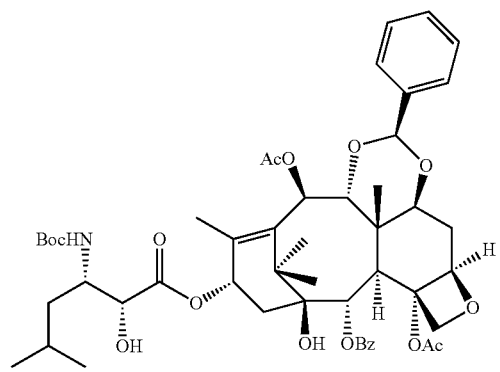

+TOF MS: m/z 920.4224 [M+H]

Example 7

7,9-acetal/ketal analogs of the 10-alpha abeo-taxanes can be prepared from the corresponding diol 15a.0 which was prepared by acetal deprotection of compound 15a.2 as outlined below.

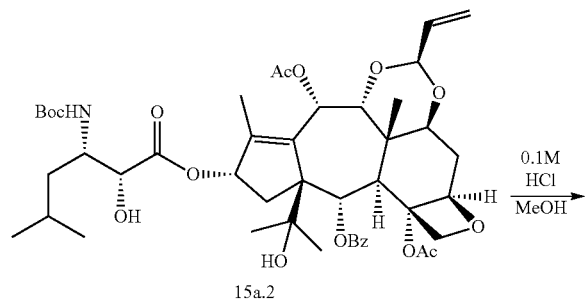

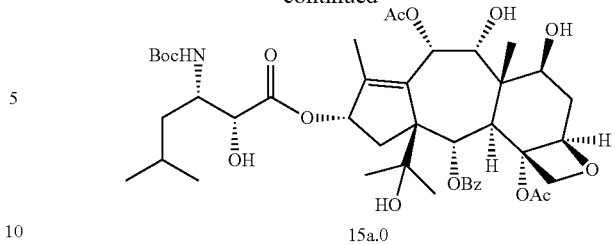

Acetal Deprotection of 10-Alpha Abeo-Taxane:

2.2 g of the acrolein acetal 15a.2 (2.53 mmol) was weighed into a 250 ml RB flask with a reflux condenser, and 50 ml (0.05 M) of MeOH was added and the mixture stirred under nitrogen. The flask warmed to 35° C.±4° C. and 16.6 ml (⅓ of MeOH volume) 0.1 N HCl was added dropwise over a period of 5 minutes and stirred over night to complete the reaction. MeOH was evaporated on a rotary evaporator and the reaction mixture was poured in saturated $NaHCO_3$ (50 ml) and extracted twice with 40 ml of EtOAc. The organic layers were combined, washed with 30 ml of brine and concentrated to give crude product which was purified by flash chromatography on silica gel using 3:7 hexanes:EtOAc to give 1.74 g of 15a.0 in 83% yield.

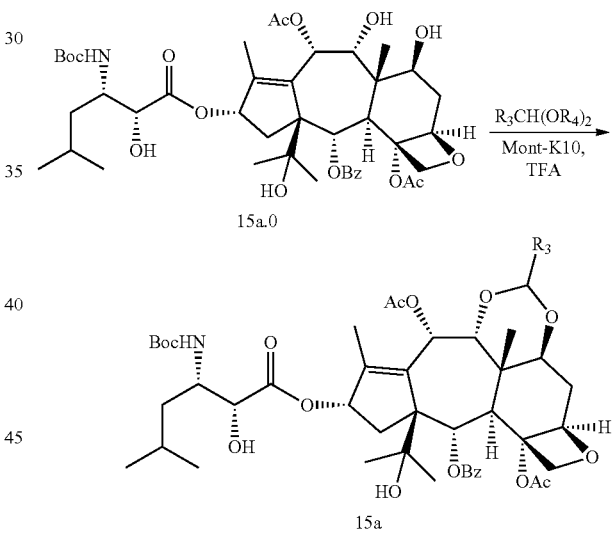

Acid Catalyzed Acetal/Ketal Formation of 10-Alpha Abeo-Taxanes:

25 mg of 15a.0 (0.03 mmol), 5 mg montmorillonite-K10 and 0.4 mmol of the corresponding dimethyl/diethyl acetal were weighed in an oven dried reaction flask equipped with a septa or a 4 ml vial with a Teflon cap. 1 ml of acetonitrile was added and the reaction mixture was stirred under nitrogen. The pH of the reaction was about 6. 1 to 2 microliters of TFA was added to bring the reaction pH to 3-3.5. The reaction mixture was stirred about 2 to 5 hours and then quenched with 2 ml of aqueous sodium bicarbonate and the solution was filtered over a bed of celite, and washed with 3×5 ml of ACN, and the filtrates combined and concentrated on the rotavapor. The crude product was purified by flash column chromatography on silica gel using heptanes/EtOAc solvent system. The following acetals/ketals 15a have been prepared employing the above general procedure in good yields (60-90%). All the compounds were characterized by the ¹H NMR and HRMS and their purity was determined by HPLC.

10-alpha abeo-taxane-2-methylpropenyl acetal (15a.3)

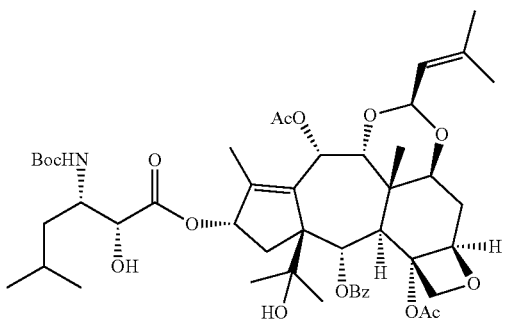

+TOF MS: m/z 915.4571 [M+18]

10-alpha abeo-taxane-2,6-dimethyl-1,5-heptadienyl acetal (15a.4)

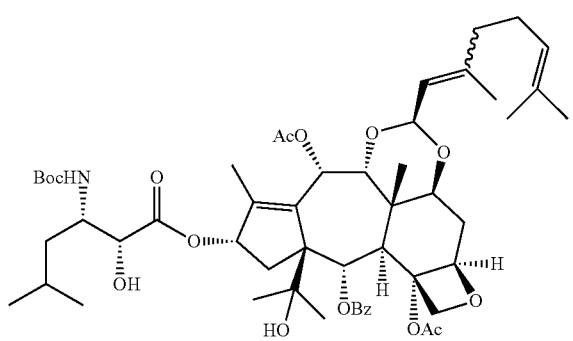

+TOF MS: m/z 983.5178 [M+18]

10-alpha abeo-taxane benzylidene acetal (15a.5)

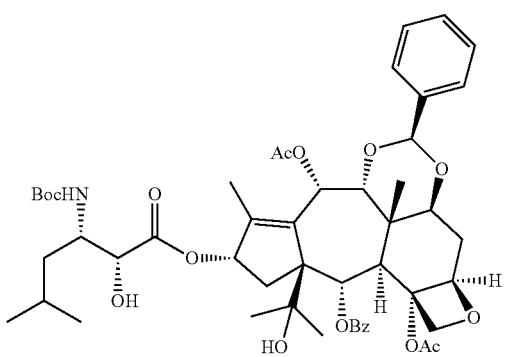

+TOF MS: m/z 937.4593 [M+18]

The MTT Proliferation Assay:

The purpose of these experiments was to compare the cytotoxicity of the abeo-taxane analogs and their normal taxane analogs listed below in multidrug resistant cells and their parental susceptible lines to show that a subset of these compounds would exhibit a similar level of toxicity in the drug resistant lines as that observed in the parent susceptible cell line.

Methods

MTT-based cytotoxicity assays were performed using human cancer cell lines and paired sublines exhibiting multidrug resistance. These lines included a uterine sarcoma line, MES-SA. (Harker, W. G.; MacKintosh, F. R.; Sikic, B. I., Development and characterization of a human sarcoma cell line, MES-SA, sensitive to multiple drugs. Cancer Res. 1983, 43, 4943-4950), and its doxorubicin-resistant subline, MES-SA/Dx5. (Harker, W. G.; Sikic, B. I., Multidrug (pleiotropic) resistance in doxorubicin-selected variants of the human sarcoma cell line MES-SA. Cancer Res. 1985, 45, 4091-4096). MES-SA/Dx5 exhibits a marked cross resistance to a number of chemotherapeutic agents including vinblastine, taxol, colchicine, vincristine, etoposide, dactinomycin, mitoxantrone and daunorubicin and moderate cross resistance to mitomycin C and melphalan. However, resistance to bleomycin, cisplatin, carmustine, 5-fluorouracil or methotrexate is not observed. MES-SA/Dx5 cells express high levels of ABCB1 (MDR1) mRNA and its gene product, the P-glycoprotein. MES-SA and MES-SA/Dx5 were purchased from the American Type Culture Collection (ATCC, Manassas, Va.).

The second set of cells tested, CCRF-CEM or simply CEM, were derived from the blood of a patient with acute lymphoblastic leukemia. (Foley, G. E.; Lazarus, H.; Farber, S.; Uzman, B. G.; Boone, B. A.; McCarthy, R. E., Continuous Culture of Human Lymphoblasts from Peripheral Blood of a Child with Acute Leukemia. Cancer 1965, 18, 522-529). The subline CEM/VLB$_{100}$ was developed to be resistant to up to vinblastine at 100 ng/ml. (Beck, W. T.; Mueller, T. J.; Tanzer, L. R., Altered surface membrane glycoproteins in Vinca alkaloid-resistant human leukemic lymphoblasts. Cancer Res. 1979, 39, 2070-2076). Drug resistance is achieved by overexpression of the MDR1 gene. Resistance in the CEM subline designated CEM/VM-1-5, however, is "atypical." (Danks, M. K.; Yalowich, J. C.; Beck, W. T., Atypical multiple drug resistance in a human leukemic cell line selected for resistance to teniposide (VM-26). Cancer Res. 1987, 47, 1297-1301). The classes of drugs included in the "classic" multiple drug resistance phenotype are Vinca alkaloids, anthracyclines, epipodophyllotoxins and antibiotics. However, CEM/VM-1-5 cells retain sensitivity to the Vinca alkaloids despite resistance and cross-resistance to etoposide, anthracyclines and mitoxantrone. (Danks, M. K.; Schmidt, C. A.; Cirtain, M. C.; Suttle, D. P.; Beck, W. T., Altered catalytic activity of and DNA cleavage by DNA topoisomerase II from human leukemic cells selected for resistance to VM-26. Biochemistry 1988, 27, 8861-8869). Resistance in CEM/VM-1-5 cells is effected by over expression of the ABCC1 (MRP1) gene. CEM, CEM/VLB$_{100}$ and CEM/VM-1-5 cells were obtained from Dr. W T Beck, University of Illinois at Chicago.

Summary of Test Compounds at Different Concentrations:

| Compound | Test Concentrations (ng/ml) |
| --- | --- |
| Paclitaxel | 25,000, 5,000, 1,000, 200, 40, 8 |
| 10-βTX (14b.2) | 1,000, 200, 40, 8, 1.6, 0.32 |
| 10-βAT (15b.2) | 25,000, 5,000, 1,000, 200, 40, 8, 1.6 |
| 10-αAT (15a.2) | 1,000, 200, 40, 8, 1.6, 0.32 |
| 10-DAB III (16) | 25,000, 5,000, 1,000, 200, 40, 8 |
| 10-αTX (14a.2) | 1,000, 200, 40, 8, 1.6, 0.32 |

Results

| Compound | MES-SA | MES-SA/Dx5 | Degree of resistance[1] | CEM | CEM/VLB$_{100}$ | Degree of resistance[2] | CEM/VM-1-5 | Degree of resistance[2] |
|---|---|---|---|---|---|---|---|---|
| Paclitaxel | 9 ± 7 | 19398 ± 204 | 3105 ± 2416 | <11/2 | 3029/1295 | >275/648 | <11/8 | 4 |
| 10-βTX (14b.2) | 28 ± 16 | 36 ± 34 | 1.2 ± 0.5 | 7.5 ± 0.7 | 22 ± 11 | 3 ± 1 | 9 ± 1 | 1.2 ± 0.3 |
| 10-βAT (15b.2) | 432 ± 261 | 328 ± 173 173 | 0.75 ± 0.07 | 112 ± 60 60 | 453 ± 293 | 4 ± 0.3 | 77 ± 6 | 0.9 ± 0.5 |
| 10-αAT (15a.2) | 9.5 ± 0.7 | 15 ± 8 | 1.6 ± 0.8 | 5 ± 3 | 19 ± 9 | 4 ± 0 | 5 ± 4 | 1.3 ± 1.4 |
| 10-DAB III (16) | N/A | N/A | N/A | N/A | N/A | N/A | N/A | N/A |
| 10-αTX (14a.2) | 30 ± 14 | 34 ± 24 | 1.1 ± 0.3 | 14 ± 5 | 43 ± 23 | 3 ± 0.6 | <0.3/15 | <0.02/1.5 |
| Vinblastine | 1.1 ± 0.3 | 43 ± 12 | 38.5 ± 0.7 | 1 ± 0.8 | 227 ± 77 | 255 ± 127 | 1.3 ± 0.9 | 1.2 ± 0.07 |
| Doxorubicin | 2 | 97 | 49 | 14 | 2100 | 150 | 3060 | 219 |

Data are expressed as IC$_{50}$ values (nM).
N/A means not active.
[1]Calculated by dividing the IC$_{50}$ of the resistant lines by the IC$_{50}$ of the sensitive MES-SA cells.
[2]Calculated by dividing the IC$_{50}$ of the resistant lines by the IC$_{50}$ of the sensitive CEM cells.

The MTS Proliferation Assay:

Day 1: Cells were plated in appropriate growth medium at $5 \times 10^3$ per well in 100 µL in 96 well tissue culture plates, Falcon, one plate for each drug to be tested. Column 1 was blank; it contained medium, but no cells. The plates were incubated overnight at 37° C. in 5% $CO_2$ to allow attachment. Day 2: Drug diluted in culture media was added to the cells at a concentration of 0.005 nM to 10 µM in quadruplicate. After 48-72 hours of drug exposure, the MTS agent was added to all wells and incubated 1-6 hrs (37° C., 5% $CO_2$), depending on cell type, as per CellTiter 96® AQueous Non-Radioactive Cell Proliferation Assay (MTS), Promega. Plates were processed using a Bio-Tek Synergy HT Multi-detection microtiter plate reader at 490 nanometer wavelength and data were processed with KC4V.3 software. Data plots of drug concentration vs. absorbance were plotted and IC$_{50}$ values were extrapolated for each of the tested compounds.

As summarized below, the IC$_{50}$ value for each tested compound in each of the various cell lines was determined. The clinical comparator drug, paclitaxel, was included in the experiment to allow comparison of the results of the candidate compounds to a clinically relevant standard in the taxane class.

The results of all the compounds tested gave a wide range of IC$_{50}$ values, some of which were extrapolated from outside the actual range of drug tested and are thus represented as <0.002 nM. The MDR negative cell lines KB, SKNAS, DU145, MDAMB435s, and the HT29 are all cell lines sensitive to paclitaxel with IC$_{50}$<0.002 nM, while the MDR positive cell lines, KBV, MV522/Mdr1, MESSA/DOX are much less sensitive to paclitaxel and have IC$_{50}$ values of 500 nM and higher.

These results are consistent with published studies where paclitaxel has been shown to be a good substrate for the MDR1 drug efflux pump, thus requiring significantly higher drug levels to reach equivalent cell cytotoxicity in MDR positive cell lines as compared to MDR-cell lines. As shown by the results for the abeo-taxane 15a.2, the compounds of the present application provide similar cytotoxicity to cancer cell lines, both MDR expressing and non-MDR expressing, with IC$_{50}$'s of less than 1 micromolar. Accordingly, the compounds of the present application are shown to be active anticancer agents.

Cytotoxicity Data:

| | MTS-6: 72 hr proliferation IC$_{50}$ nM | | |
|---|---|---|---|
| Cell type | | 10alphaAT (15a.2) | Paclitaxel | 10betaAT (15b.2) |
| A2780-A5 | | 0.282 | <0.002 | * |
| A2780-DXR1 | (MDR+) | 15 | 3582 | * |
| HCT-15 | (MDR+) | 2.4 | 311 | * |
| MDAH2774 | | 0.18 | 0.015 | * |
| MV522 | | 3.5 | 1.71 | * |
| 22Rv1 | | 5.7 | 1.7 | * |

* IC$_{50}$ nM Cytotoxic data for 10betaAT are determined to be in the similar magnitude as those obtained from 10alphaAT.

Example 4

In one embodiment, the tubulin protein assembly assay was conducted according to the procedures as described by Mathew A E, Mejillano M R, Nath J P, Himes R H, Stella V J, "Synthesis and Evaluation of Some Water-Soluble Prodrugs and Derivatives of Taxol with Antitumor Activity", J. Med. Chem., 35, 145-151 (1992) and Georg G I, Cheruvallath Z S, Himes R H, Mejillano M R, Burke C T, "Synthesis of Biologically Active Taxol Analogs with Modified Phenylisoserine Side Chains", J. Med. Chem., 35, 4230 (1992).
The data are provided below:

| Compound | ED50, µM | ED50/ED50 (Paclitaxel) |
|---|---|---|
| Paclitaxel | 2.97 ± 0.50 | 1.00 |
| Docetaxel | 3.18 ± 0.45 | 1.07 |
| Epothilone B | 3.31 ± 0.51 | 1.11 |
| 10alphaAT (15a.2) | 1.58 ± 0.46 | 0.53 |
| 10betaAT (15b.2) | * | * |
| 10alphaTX (14a.2) | * | * |
| 10betaTX (14b.2) | * | * |

* ED50 and ED50/ED50 (Paclitaxel) data for 10betaAT, 10alphaTX and 10betaTX are determined to be in the magnitude of 10alphaAT.

As in the case of the cytotoxicity results, the abeo-taxane analog 15a.2 demonstrates surprisingly great affinity for tubulin in this binding assay protocol compared to several recognized tubulin binding agents. The additional compounds of the present application similarly are expected to show high affinity for tubulin making them potentially useful as anticancer drugs like paclitaxel or as prospective drugs for treating other tau and tubulin associated disorders.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope.

The entire disclosures of all documents cited throughout this application are incorporated herein by reference.

What is claimed is:

1. A compound of the formula:

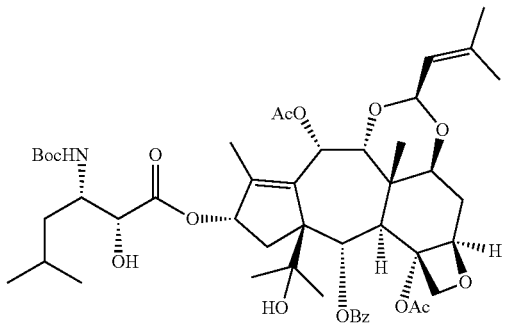

and
pharmaceutically acceptable salts thereof.

2. The compound of claim 1, wherein the compound is greater than 95% pure or greater than 99% pure.

3. A pharmaceutical composition comprising:
 a) a therapeutically effective amount of a compound of claim 1, in the form of a single diastereoisomer; and
 b) at least one pharmaceutically acceptable excipient, diluent or adjuvant.

4. The composition of claim 3 further comprising temozolomide and/or Avastin.

5. The composition of claim 3, further comprising one or more therapeutic agent selected from the group consisting of aromatase inhibitors, antiestrogen, anti-androgen, a gonadorelin agonists, topoisomerase 1 inhibitors, topoisomerase 2 inhibitors, microtubule active agents, alkylating agents, anthracyclines, corticosteroids, IMiDs, protease inhibitors, IGF-1 inhibitors, CD40 antibodies, Smac mimetics, FGF3 modulators, mTOR inhibitors, HDAC inhibitors, IKK inhibitors, P38MAPK inhibitors, HSP90 inhibitors, akt inhibitors, antineoplastic agents, antimetabolites, platin containing compounds, lipid- or protein kinase-targeting agents, protein- or lipid phosphatase-targeting agents, anti-angiogentic agents, agents that induce cell differentiation, bradykinin 1 receptor antagonists, angiotensin II antagonists, cyclooxygenase inhibitors, heparanase inhibitors, lymphokine inhibitors, cytokine inhibitors, bisphosphanates, rapamycin derivatives, anti-apoptotic pathway inhibitors, apoptotic pathway agonists, PPAR agonists, inhibitors of Ras isoforms, telomerase inhibitors, protease inhibitors, metalloproteinase inhibitors and aminopeptidase inhibitors, cytostatic agent, cytotoxic agent, taxane, topoisomerase II inhibitor, topoisomerase I inhibitor, tubulin interacting agent, antibodies, antiangiogenics, COX-2 inhibitors, hormonal agent, thymidilate synthase inhibitor, anti-metabolite, alkylating agent, farnesyl protein transferase inhibitor, signal transduction inhibitor, EGFR kinase inhibitor, antibody to EGFR, C-abl kinase inhibitor, hormonal therapy combination and aromatase combination.

* * * * *